(12) United States Patent
Loh et al.

(10) Patent No.: US 6,855,536 B2
(45) Date of Patent: Feb. 15, 2005

(54) MATERIALS AND METHODS FOR THE ENHANCEMENT OF EFFECTIVE ROOT NODULATION IN LEGUMES

(75) Inventors: John T. Loh, Knoxville, TN (US); Gary Stacey, Knoxville, TN (US)

(73) Assignee: University of Tennessee Research Corp., Inc., Knoxville, TN (US)

( * ) Notice: Subject to any disclaimer, the term of this patent is extended or adjusted under 35 U.S.C. 154(b) by 118 days.

(21) Appl. No.: 09/909,735

(22) Filed: Jul. 20, 2001

(65) Prior Publication Data

US 2002/0058327 A1 May 16, 2002

Related U.S. Application Data

(60) Provisional application No. 60/219,509, filed on Jul. 20, 2000.

(51) Int. Cl.[7] .............................................. A01N 63/00
(52) U.S. Cl. ................................ 435/252.2; 435/252.1; 435/253.6; 435/244; 47/58.1; 504/117
(58) Field of Search .............................. 435/252.1, 244, 435/252.2, 253.6; 47/58.1; 504/117

(56) References Cited

U.S. PATENT DOCUMENTS

| | | | |
|---|---|---|---|
| 4,535,061 A | 8/1985 | Chakrabarty | |
| 5,173,424 A | 12/1992 | Stacey | |
| 5,432,079 A | 7/1995 | Johansen et al. | |
| 5,695,541 A | 12/1997 | Kosanke | |
| 5,916,029 A | 6/1999 | Smith | |

FOREIGN PATENT DOCUMENTS

| | | |
|---|---|---|
| JP | 09224654 | 9/1997 |
| WO | WO 99/27786 | 6/1999 |

OTHER PUBLICATIONS

Fuhrmann, J. and A.G. Wollum II [1989] "Nodulation competition among *Bradyrhizobium japonicum* strains as influenced by rhizosphere bacteria and iron availability", *Biology and Fertility of Soils*, 7:108–112, Springer–Verlag.

Grob et al. [1993] "A novel response–regulator is able to suppress the nodulation defect of a *Bradyrhizobium japonicum* nodW mutant", *Mol. Gen. Genet.* 241:531–541, Springer–Verlag.

Lesueur et al. [1993] "Iron requirement and siderophore production in *bradyrhizobium* strains isolated from *Acacia mangium*", *Journal of Applied Bacteriology*, 74: 675–682.

Van Rossum et al. [1994] "Siderophore production by *Bradyrhizobium* spp. strains nodulating groundnut", *Plant and Soil*, 163:177–187, Kluwer Academic Publishers, Netherlands.

Kleerebezem et al. [1997] "Quorum sensing by peptide pheromones and two–component signal–transduction systems in Gram–positive bacteria," *Mol. Microbiol.* 24(5):895–904, Blackwell Science Ltd.

Loh et al. [2002] "A Two–Component Regulator Mediates Population–Density–Dependent Expression of the *Bradyrhizobium japonicum* Nodulation Genes," *J. Bacteriol.* 184(6):1–8.

Loh, J.T. and G. Stacey [2001] "Feedback regulation of the *Bradyrhizobium japonicum* nodulation genes," *Mol. Microbiol.* 41(6): 1357–1364, Blackwell Science Ltd.

Loh et al. [2001] "Population density–dependent regulation of the *Bradyrhizobium japonicum* nodulation genes," *Mol. Microbiol.* 42(1):37–46, Blackwell Science Ltd.

Loh et al. [1999] "The *Bradyrhizobium japonicum* nolA Gene Encodes Three Functionally Distinct Proteins," *J. Bacteriol.* 181(5):1544–1554, American Society for Microbiology.

Loh et al. [1997] "NodV and NodW, a Second Flavonoid Recognition System Regulating nod Gene Expression in *Bradyrhizobium japonicum*," *J. Bacteriol.* 179(9):3013–3020, American Society for Microbiology.

Nieuwkoop et al. [1987] "A Locus Encoding Host Range is Linked to the Common Nodulation Genes of *Bradyrhizobium japonicum*," *J. Bacteriol.* 169(6):2631–2638, American Society for Microbiology.

Rosemeyer et al. [1998] "luxI– and luxR–Homologous Genes of *Rhizobium* etli CNPAF512 Contribute to Synthesis of Autoinducer Molecules and Nodulation of *Phaseolus vulgaris*," J. Bacteriol. 180(4):815–821, American Society for Microbiology.

Sadowsky et al. [1991] "The *Bradyrhizobium japonicum* nolA gene and its involvement in the genotype–specific nodulation of soybeans," Proc. Natl. Acad Sci. USA 88:637–641.

Thome and Williams [1999] "Cell Density–Dependent Starvation Survival of *Rhizobium leguminosarum* bv. phaseoli: Identification of the Role of an N–Acyl Homoserine Lactone in Adaptation in Staionary–Phase Survival," J. Bacteriol. 181(3):981–990, American Society for Microbiology.

van Brussel et al. [1985] "Bacteriocin small of Fast–Growing Rhizobia is Chloroform Soluble and is not Required for Effective Nodulation," J. Batceriol. 162(3):1079–1082, American Society for Microbiology.

Van Rossum et al. [1994] "Siderophore production by Bradyrhizobium spp. strains nodulating groundnut", Plant and Soil, 163:177–187, Kluwer Academic Publishers, Netherlands.

(List continued on next page.)

*Primary Examiner*—Leon B. Lankford, Jr.
(74) *Attorney, Agent, or Firm*—Saliwanchik, Lloyd & Saliwanchik

(57) ABSTRACT

The subject invention relates to compounds and compositions which induce transcripts of the nolA gene in nitrogen-fixing bacteria, such as *Bradyrhizobium japonicum*. Novel bacterial strains which are insensitive too NolA, soil inoculants comprising NolA insensitive bacteria and/or nolA inducers, and methods of increasing nitrogen fixation in legumes are also disclosed.

9 Claims, 22 Drawing Sheets

OTHER PUBLICATIONS

Wijffelman et al. [1983] "Repression of Small Bacteriocin Excretion in *Rhizobium Leguminosarum* and *Rhizobium trifolii* by Transmissible Plasmids," *Mol. Gen. Genet.* 192: 171–176, Springer–Verlag.

Yuen, J.P. and G. Stacey [1996] "Inhibition of nod Gene Expression in *Bradyrhizobium japonicum* by Organic Acids," *Mol. Plant–Microbe Interact.* 9(5):424–428, The American Phytopathological Society.

Banfalvi et al. [1988] "Regulation of nod gene Expression in *Bradyrhizobium japonicum,"Mol. Gen. Genet.* 214:420–424, Springer–Verlag.

Cha et al. [1998] "Production of Acyl–Homoserine Lactone Quorum–Sensing Signals by Gram–Negative Plant–Associated Bacteria," *Mol. Plant Microbe Int*11(11):1119–1129, The American Phytopathological Society.

Cubo et al. [1992] "Molecular Characterization and Regulation of the Rhizosphere–Expressed Genes rhiABCR That Can Influence Nodulation by *Rhizobium leguminosarum* Biovar viciae," *J. Bacteriol.* 174–4026–4035, American Society for Microbiology.

Dockendorff et al. [1994]"NoIA Represses nod Gene Expression in *Bradyrhizobium japonicum,"* *Mol. Plant–Microbe Interact.* 7(65):596–602, The American Phytopathological Society.

Fellay et al. [1998] "nodD2 of Rhizobium sp. NGR234 is involved in the repression of the nodABC operon," *Mol. Microbiol.* 27(5):1039–1050, Blackwell Science Ltd.

Fuqua, W.C., et al. [1994] "Quorum Sensing in Bacteria: The LuxR–Luxi Family of Cell Density–Responsive Transcriptional Regulators," *J. Bacteriol.* 176(2):269–275, American Society for Microbiology.

Fuqua, W.C. and S.C. Winans [1994] "A LuxR–LuxI Type Regulatory System Activates Agrobacterium Ti Plasmid Conjugal Transfer in the Presence of a Plant Tumor Metabolite," *J. Bacteriol.* 176(10):2796–2808, American Society for Microbiology.

Garcia, M.L., et al. [1996] "Phenotypic Characterization and Regulation of the noIA gene of *Bradyrhizobium japonicum,"* *Mol. Plant–Microbe Interact* 9(7):625–635, The American Phytopathological Society.

Gillette, W.K. and G. H. Elkan [1996] "Bradyrhizobium (Arachis) sp. Strain NC92 Contains Two nodD Genes Involved in the Repression of nodA and a noIA Gene Required for the Efficient Nodulation of Host Plants," *J. Bacteriol.* 178(10):2757–2766, American Society for Microbiology.

Gray et al. [1996] "Cell–to–Cell Signaling in the Symbiotic Nitrogen–Fixing Bacterium *Rhizobium leguminosarum*: Autoinduction of a Stationery Phase and Phizosphere–Expressed Genes," *J. Bacteriol.* 178(2):372–376, American Society for Microbiology.

Hardman, A.M. et al. [1998] "Quroum sensing and the cell–cell communication dependent regulation of gene expression innpathogenic and non–pathogenic bacteria," Antonie van Leeuwenhoek 74:199–210, Kluwer Academic Publishers, Netherlands.

Rosemeyer et al. [1998] "luxi– and luxR–Homologous Genes of *Rhizobium etli* CNPAF512 Contribute to Synthesis of Autoinducer Molecules and Nodulation of *Phaseolus vulgaris,"* *J. Bacteriol.* 180(4):815–821. American Society for Microbiology.

| RATIO OF NWSB:110 | % OCCUPANCY BY NWSB MUTANT | |
|---|---|---|
| | Untreated | BEHP |
| 1:10 (A) | 0 | 11 |
| (B) | 2 | 0 |
| 10:1 (A) | 83 | 95 |
| (B) | 93 | 92 |
| 1:1 (A) | 57 | 78 |
| 1:1 (B) | 40 | 74 |

Figure 15

| STRAIN | NolA-lacZ expression (fold induction) | +/- induction |
|---|---|---|
| Bradyrhizobium japonicum USDA 110 | 8.0 | +++++ |
| Rhizobium Loti NZP2037 | 3.0 | ++ |
| Rhizobium lupini | 2.8 | ++ |
| Sinorhizobium meliloti AK631 | 3.5 | ++ |
| Sinorhizobium meliloti 1021 | 2.4 | + |
| Rhizobium leguminosarum | 3.0 | ++ |
| Sinorhizobium sp. NGR234 | 3.0 | ++ |
| Pseudomonas fluorescens 5R | 0.9 | - |
| Pseudomonas fluorescens DFC50 | 0.8 | -- |
| Pseudomonas aeruginosa PAO1 | 1.0 | - |
| Pseudomonas syringae B3A | 1.1 | - |
| Pseudomonas syringae B457 | 1.2 | - |
| Pseudomonas aureofaciens Q2A7 | 1.0 | - |
| Agrobacterium GV101 | 2.7 | ++ |
| Agrobacterium LB4404 | 2.4 | + |
| Marine isolate, gamma proteobacterium (Uwo.Ps) | 1.2 | - |
| Marine isolate, gamma proteobacterium (uwo.stk) | 1.1 | - |
| Marine isolate, gamma proteobacterium (uwo.mor) | 0.9 | - |
| Aeromonas caviae | 1.8 | - |
| Vibrio harveyii | 2.4 | - |
| Vibrio natriegens | 1.3 | - |
| Vibrio splendidus | 2.5 | - |
| Rhodopseudomonas palustris | 2.7 | ++ |
| Salmonella typhi | 1.1 | - |
| Salmonella enterditis | 1.0 | - |
| Salmonella typhi 284 | 1.0 | - |
| M. smeraglitis | 1.0 | - |

FIG. 18

MATERIALS AND METHODS FOR THE ENHANCEMENT OF EFFECTIVE ROOT NODULATION IN LEGUMES

CROSS REFERENCE TO RELATED APPLICATIONS

This application claims priority to United States Provisional Application 60/219,509, filed Jul. 20, 2000, hereby incorporated by reference in its entirety, including the disclosure, figures, and tables.

The subject invention was made with government support under a research project supported by The National Science Foundation Grant No. IBN-972828 1. The government may have certain rights in this invention.

BACKGROUND OF THE INVENTION

Leguminous plants, such as soybeans, are able to fix nitrogen from the atmosphere due to a symbiotic relationship between the plants and bacteria which dwell in nodules formed in the roots of the plants. Specifically, soil bacteria that are members of the family Rhizobiaceae, are capable of infecting plants and inducing highly differentiated root nodule structures within which atmospheric nitrogen is reduced to ammonia by the bacteria. The host plant utilizes the ammonia as a source of nitrogen. The symbiotic root nodule bacteria are classified in several separate genera, including Rhizobium, Bradyrhizobium, Sinorhizobium, and Azorhizobium.

Legume nodulation by rhizobia exhibits some species specificity. Bradyrhizobium species include the commercially important soybean nodulating strains *B. japonicum* (i.e., strains USDA 110 and 123), promiscuous rhizobia of the cowpea group, and *B. parasponia* (formerly *Parasponia rhizobium*) which nodulates the non-legume Parasponia, as well as a number of tropical legumes, including cowpea and siratro. The most important agricultural host of *B. japonicum* is soybean (*Glycine max*), but this bacterium will nodulate a few other legumes (e.g., cowpea and siratro). Fast growing rhizobia include, among others, *Rhizobium etli*, *Sinorhizobium meliloti* (formerly *Rhizobium meliloti*), and *Rhizobium leguminosarum biovar trifolii*, which nodulate bean, alfalfa, and clover, respectively. These *Rhizobium* species generally display a narrow host range. However, *Rhizobium* sp. NGR234 has the ability to nodulate over 100 genera of legumes. *Sinorhizobium fredii* (formerly *Rhizobium fredii*), is phylogenetically distinct from *B. japonicum*, but has the ability to nodulate *Glycine soja* (a wild soybean species), *G. max* cv. Peking, and a few other soybean cultivars.

There are currently about 70,000,000 acres of soybean grown in the United States. An inoculant industry exists to sell *B. japonicum* to farmers for incorporation into the soil during soybean planting. The use of these inoculants is intended to enhance the efficiency of nitrogen fixation. Unfortunately, for most of the United States, inoculation has been shown to be ineffective. Therefore, the inoculant industry remains relatively small (approximately $20–30 million per year). Indeed, at present, inoculation is only recommended for newly planted fields (i.e., those not planted with soybeans previously) and fields that have been out of production for over three years.

The primary reason for the inefficiency of soil inoculation is the presence of competing extant *B. japonicum* in soil. When a field has been producing soybean for more than one season, there is a build up of the *B. japonicum* populations in soil. These bacteria are highly competitive since they have adapted to their soil environment. Hence, when the inoculant is added, the indigenous soil *B. japonicum* strains compete and win the battle to nodulate the plant. The result is that, in many cases, less than 1% of the nodules formed on the planted soybean are due to the inoculant added. Therefore, even if a high-yielding *B. japonicum* strain is used as the inoculant, the farmer does not see the yield increase due to the fact that the inoculant has not found its way into the plant.

In the major soybean growing areas of the Midwest, the most competitive population of *B. japonicum* is that of serogroup 123. If improvement in the nitrogen fixing capacity of the soybean-*Bradyrhizobium* symbiosis through application of superior strains is to be realized, then the difficult problem of competition from indigenous populations (such as serogroup 123) will have to be solved.

Significant efforts have been made to understand and alter the competitiveness of indigenous Bradyrhizobia. For example, attempts to alter soybean nodule occupancy ratios of indigenous versus applied Bradyrhizobia have been reported. However, such alterations were only achieved by using ultra-high, economically infeasible rates of the applied strain. In a seven year study, Dunigan et al. [Agron. J. 76: 463–466 (1984)] demonstrated that the inoculant strain USDA 110 eventually formed the majority of nodules after high rates of application in the first 2 years (serogroup 123 was not among the indigenous population). However, the tenacious competitive ability of serogroup 123 appears not to be related to numbers per se and when normal rates of inoculant are applied the indigenous serogroup 123 population can still form up to 95% of the nodules on soybean.

The formation of nodules on leguminous plants involves a complex exchange and recognition of diffusible signals between the plant and the bacterial symbiont. A key plant signal are the flavonoids which trigger the induction of the bacterial nodulation genes (Day et al. [2000] In: Prokaryotic Nitrogen Fixation: A Model System for the Analysis of a Biological Process, ed. Triplett, E., Horizon Scientific Press, Norfolk, England, pp 385–414).

Nodulation genes of *Bradyrhizobium* and *Rhizobium* strains affect the early stages of nodule formation including host-bacterium recognition, infection and nodule development. Wild type strains of *Bradyrhizobium* species display some variation in these early nodulation steps which is reflected in differences in relative rates of initiation of nodulation and ultimately in differences in competitiveness between strains for nodule occupancy. For example, *B. japonicum* USDA 123 is believed to be more competitive for nodulation than *B. japonicum* USDA 110. Strains which initiate infection and nodules earlier will occupy a greater portion of the nodules on a given plant. Improving the competitiveness of a specific Bradyrhizobium is an important part of the development of improved inoculants for legumes. A more effective Bradyrhizobium strain must be able to out-compete the indigenous rhizobia population for nodule occupancy in order for their improved qualities to impact on the inoculated legume. Therefore, there is a significant need for an inoculating composition and/or an inoculating method which would improve competitiveness of a selected inoculant strain.

In the *Bradyrhizobium japonicum*-soybean symbiosis, several key regulatory components have been identified in the regulation of bacterial nodulation genes. Two of these, i.e., a LysR regulator, $NodD_1$ and a two component regulatory system, NodWV are known to positively activate the *B. japonicum* nodulation genes in response to the plant produced isoflavonoids, genistein and daidzein. A third regulatory component (i.e., NolA) is a MerR type regulator (Sadowsky et al. [1991] *Proc. Natl. Acad Sci. USA* 88:637–641) that possesses the unique capacity to exist in three functionally distinct forms (i.e., $NolA_1$, $NolA_2$ and $NolA_3$) (Loh et al. [1999] *J. Bacteriol* . 181:1544–1554). These polypeptides are derived from alternative translation of three in-frame initiation codons.

Induction of the *B. japonicum* nolA gene leads to the subsequent repression of the nodulation genes in this bacterium. The products of the nodulation genes are required for soybean nodulation. Thus, these plant compounds, by inducing nolA expression, lead eventually to an inhibition of nodulation.

$NolA_1$ is required for the expression of both $NolA_2$ and $NolA_3$. Two transcriptional (P1 and P2) start sites have been identified (Loh et al. [1999] *J. Bacteriol.* 181:1544–1554). Transcription from P1 results in the formation of an mRNA encoding $NolA_1$. $NolA_1$ then regulates transcription from P2, resulting in the expression of both $NolA_2$ and $NolA_3$.

Although NolA is involved in the negative control of the nodulation genes (Dockendorff, T. C., J. Sanjuan, P. Grob, and G. Stacey [1994] *Mol. Plant-Microbe Interact.* 7:596–602), current information suggests that NolA does not act directly to repress nod gene expression. This view is supported by the observation that while expression of NolA from a multicopy plasmid resulted in a reduction of nod gene expression, interposon mutations to the nolA gene did not lead to elevated levels of nod gene expression (Garcia, M. L., J. Dunlap, J. Loh, and G. Stacey [1996] *Mol. Plant-Microbe Interact* 9:625–635). In fact, NolA appears to positively regulate the expression of $NodD_2$, the latter of which has been shown to be a repressor of the nod genes in Rhizobium spp. NGR234, *Bradyrhizobium* spp. (*Arachis*) NC92 and *Bradyrhizobium japonicum* (Garcia, M. L., J. Dunlap, J. Loh, and G. Stacey [1996] *Mol. Plant-Microbe Interact* 9:625–635; Gillette, W. K. and G. H. Elkan [1996] *J. Bacteriol* . 178:2757–2766; and Fellay, R., M. Hanin, G. Montorzi, J. Frey, C. Freiberg, W. Golinowski et al. [1998] *Mol. Microbiol.* 27:1039–1050. Therefore, NolA affects repression indirectly, through the control of $nodD_2$ expression.

Cell-cell signaling plays a large role in the ability of bacteria to respond and adapt to a particular environment. Regulatory systems that control gene expression in response to population density (i.e., quorum sensing) govern such bacterial phenotypes as bioluminescence, antibiotic production, plasmid conjugal transfer and the synthesis of virulence factors in both plant and animal pathogens (Hardman, A. M. et al. [ 1998] *Antonie van Leeuwenhoek* 74:199–210). Quorum sensing involves the recognition of self-produced signal compounds, which function to regulate the expression of genes when threshold levels of these signals have accumulated in cultures of a sufficiently high population density. hi Gram-negative bacteria, the best studied of these signals are N-Acyl homoserine-lactones (AHL) (Fuqua, W. C. et al. [1994] *J. Bacteriol* 176:269–275). In Gram-positive bacteria, an equivalent role is played by various posttranslationally-modified peptides (Kleerebezem, M. et al. [1997] *Mol. Microbiol.* 24:895–904). Several AHL compounds have been identified from rhizobia, including *Rhizobium leguminosarum* biovars *viciae, trifoli* and *phaseoli, Rhizobium etli*, and *Rhizobium meliloti* (Thorne and Williams [1999] *J. Bacteriol.* 181:981-990; Cha et al. [1998] *Mol. Plant Microbe Int.* 11:1119–1129; Gray et al. [1996] *J. Bacterial.* 178:372–376; Rosemeyer et al. [1998] *J. Bacteriol.* 180:815–821; Van-Brussel et al. [1985] *J. Bacteriol.* 162:1079–1082; and Wijffelman et al. [1983] *Mol. Gen. Genet.* 192:171–176). In a few cases, these autoinducers have been implicated in the nodulation process. For example, the small AHL molecule produced by *R. leguminosarum* by. *viciae* is required for the expression of the rhiABC operon, which is important for rhizosphere growth and nodulation efficiency (Cubo et al. [1992] *J. Bacteriol.* 174:4026–4035). In *R. etli*, mutations that disrupt AHL synthesis resulted in decreased nodule numbers on host plants (Rosemeyer et al. [1998] *J. Bacteriol.* 180:815–821). Therefore, AHL-mediated quorum sensing may play an important role in the symbiotic process. To date, no quorum-sensing compound has been identified from the soybean symbiont *Bradyrhizobium japonicum.*

The current invention addresses the inefficiency of soil inoculation due to the presence of competing indigenous *B. japonicum* in soil and provides novel compounds and compositions which increase the efficiency of nodulation in target plants. Specifically, field inoculants comprising high-yielding NolA insensitive *B. japonicum* and nolA inducers address the long standing obstacle of inefficient nodulation due to indigenous *B. japonicum* strains.

BRIEF SUMMARY OF THE INVENTION

The subject invention provides materials and methods to improve nitrogen fixation in leguminous plants. In a preferred embodiment of the subject invention, the improvement in nitrogen fixation is achieved by providing an inoculant of nitrogen-fixing bacteria which, when applied according to the subject invention, have a competitive advantage over indigenous strains.

In a specific embodiment, the subject invention provides compounds and compositions which induce transcription of the nolA gene in nitrogen-fixing bacteria, such as *Bradyrhizobium japonicum*. By applying these NolA inducers to the situs of indigenous *B. japonicum* it is possible to induce transcription of the nolA gene in indigenous bacteria, thereby reducing the ability of these bacteria to initiate nodulation.

A further aspect of the subject invention is the identification of novel bacteria which are insensitive to NolA. In a preferred embodiment of the subject invention, these NolA insensitive microbes can be applied to legumes in conjunction with the NolA inducers of the subject invention. The NolA inducers inhibit the indigenous bacteria but do not adversely affect the nodulation capabilities of the NolA insensitive ($NolA^{INS}$) inoculant bacteria. This gives the inoculant bacteria a competitive advantage compared to the indigenous bacteria.

A further aspect of the subject invention relates to nucleic acids, expression cassettes, and vectors which encode the NolA inducer compounds of the subject invention. These genetic materials can be used to efficiently produce the inducer compounds. The inducer compounds can be produced in recombinant hosts including plants. Thus, one aspect of the subject invention concerns plants having polynucleotides which encode compounds which induce transcription of the nolA gene in nitrogen-fixing bacteria.

BRIEF DESCRIPTION OF THE DRAWINGS

FIG. 1—HPLC reverse phase chromatography (C18) of soybean seedlings extract (SSGE) fractions. Peaks collected as IND-1 and IND-2 were active on *B. japonicum* nolA-lacZ fusions.

FIG. 2A—Structure of IND-1. FIG. 2B-Effect of phthalic acid bis-(2-ethyl-hexyl) ester on nolA expression. *B. japoni-*

*cum* cells harboring a nolA-lacZ fusion were treated with increasing concentrations of the phthalate derivate, and the level of nolA expression determined.

FIG. 3—Effect of phosphatidyl inositol extract on nolA expression. Phosphatidyl inositol samples were either treated or untreated with 100 µg/ml chitinase (Sigma Chemical Co.).

FIG. 4—Analysis of soybean phosphatidyl-inositol extracts. FIG. 4A-Reverse phase comparison of extracts that had been untreated or treated with chitinase (100 µg/ml). FIG. 4B—Effect of chitinase on the ability of peak 9 to induce nolA expression.

FIG. 5–FIG. 5A depicts population density dependent expression of $nolA_{1,2,3}$-lacZ and $nodD_2$-lacZ. *B. japonicum* cultures harboring either $nolA_{1,2,3}$-lacZ, $nodD_2$-lacZ or npt-lacZ were grown to various population densities and the β-galactosidase activity of these fusions determined. Percent maximum activity is [β-galactosidase activity/maximal β-galactosidase activity of fusion]×100%. FIG. 5B—Inducer of nolA expression is population density dependent. Conditioned medium was obtained from *B. japonicum* cultures grown to various population densities and used to induce a *B. japonicum* strain harboring a $nolA_{1,2,3}$-lacZ fusion. Standard deviation was less than 10%.

FIG. 6—The inducibility of nod gene expression as a function of initial population density.

FIG. 7—Comparison of nodY-lacZ expression in a USDA110 and BjB3 (nolA mutant). *B. japonicum* cultures were grown to various population densities and the ability of 0.05 µM genistein to induce nodY expression determined. The fold induction is presented. The uninduced levels of nodY-lacZ expression in USDA110 and BjB3 were 4±1 and 3±1, respectively. Standard deviation was less than 10%.

FIG. 8—Effect of IND-1 on genistein induction of a nodY-lacZ expression in *B. japonicum*. *B. japonicum* cells harboring a nodY-lacZ fusion were incubated with increasing amounts and the ability of this compound to affect nod gene expression determined.

FIG. 9—Effect of IND-1 on $nolA_{1,2,3}$, $nolA_1$, $nolA_2$ and $nolA_3$ expression.

FIG. 10—Effect of quorum factor (i.e., conditioned medium) and IND-1 on the ability of *B. japonicum* strain USDA110 to nodulate soybean. *B. japonicum* cells were untreated (left) or incubated in conditioned medium or IND-1 for 1 h, and then inoculated onto soybean plant (107 cells per root). The number of nodules (±standard error) was determined 21 days post-inoculation, both above the mark (i.e., upper zone), or below the mark (new tissue) at the time of inoculation (n=number of plants per treatment).

FIG. 11A–C—The expression of $nodD_2$-lacZ and nolA-lacZ fusions as a function of *B. japonicum* culture density was examined (FIG. 11A). $NolA_1$ expression is cell-density dependent and required for $NodD_2$ expression (FIG. 11B). The ability of the conditioned medium to induce the nolA fusions was population density dependent with little or no induction of the fusions observed using conditioned medium derived from cultures of $A_{600}<0.2$ (FIG. 11C).

FIG. 12—HPLC isolation of Cell Density Factor (Quorum Factor) from *B. japonicum* conditioned medium (concentrated approximately 10-fold). Quorum factor containing material was applied to a C18 column (Phenomenex, Inc., Torrance, Calif.) and eluted with a methanol gradient (0–100%) at a flow rate of 1 mL per minute. Cell density factor was demonstrated to be a potent inducer of nolA expression.

FIG. 13—FIG. 13 provides a graphical depiction of the invention.

FIGS. 14A–B illustrate the effect of $FeCl_3$ on nolA-lacZ expression. *B. japonicum* cells harboring a nolA-lacZ fusion were treated with increasing concentrations of $FeCl_3$ for five hours and the level of nolA expression was determined (FIG. 14A). FIG. 14B demonstrates an increase in the expression of a nodY-lacZ fusion protein when cells are grown in the presence of iron. *B. japonicum* cells containing a nodY-lazZ fusion were induced for five hours with 0.025 µM genistein in the presence or absence of 500 µM $FeCl_3$.

FIG. 15 shows the effect of bis-(2-ethyl-hexyl) ester phthlate (BEHP) on nodule occupancy by the NwsB mutant. Different ratios of *B. japonicum* USDA110 and *B. japonicum* NwsB mutant were innoculated on soybean plants grown in growth pouches. At the time of innoculation, the root tip (RT) mark was noted on the outside of the pouches. Nodules were extracted 21 days post innoculation and the extracts were plated on RDY plates. Single colonies were picked and tested for streptomycin resistance (a marker for the NwsB mutant). (A) is above RT at time of innoculation; (B) below RT at time of innoculation.

FIGS. 17–18 illustrates the expression of CDF or quorum factor-like molecules in a variety of other bacteria.

DETAILED DISCLOSURE OF THE INVENTION

Figure 1:
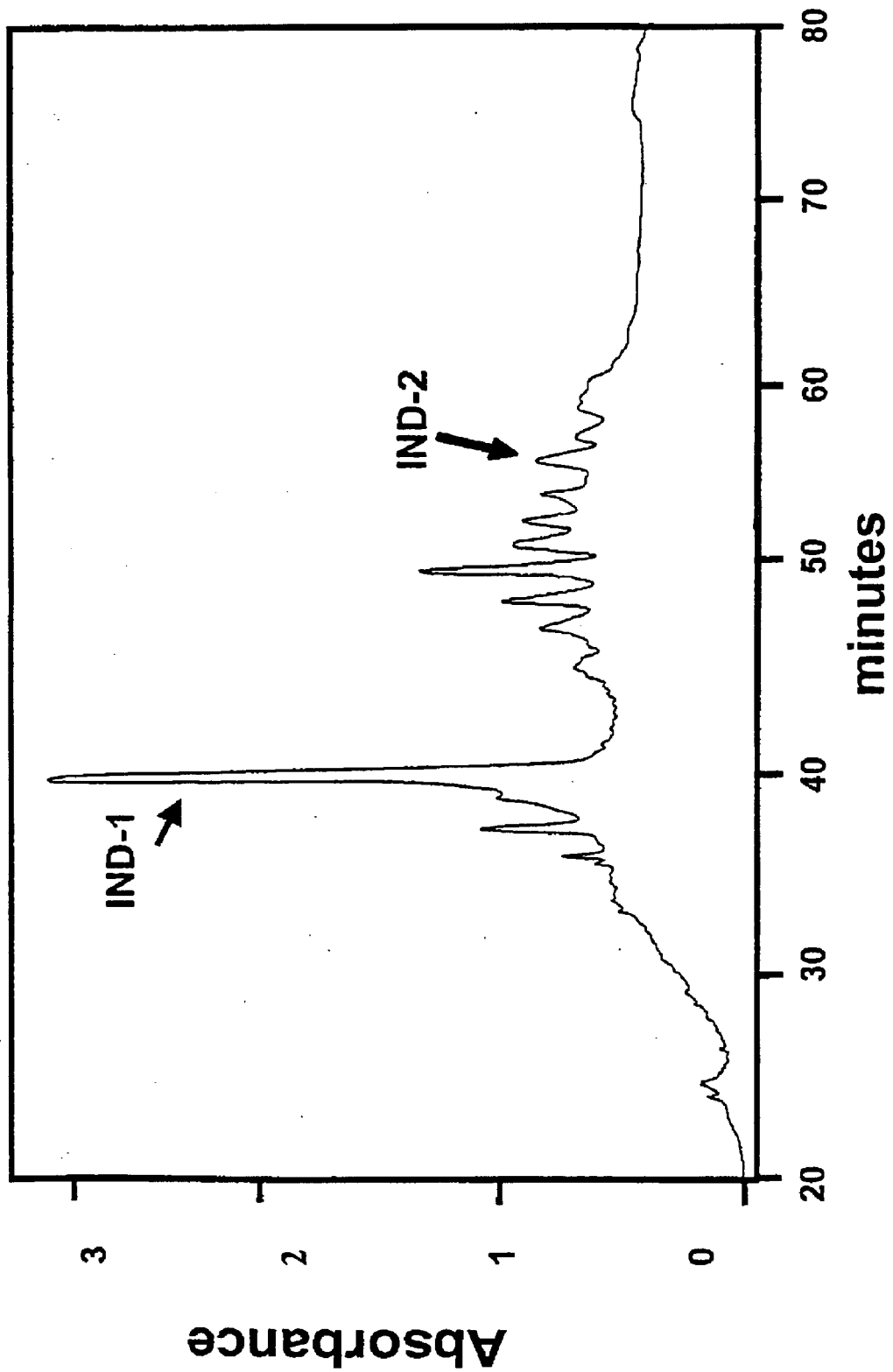

The subject invention provides materials and methods for promoting the growth of leguminous plants by enhancing the efficiency of root nodulation by nitrogen-fixing bacteria. This enhancement of nodulation efficiency is achieved by providing high-performing inoculant bacteria with a competitive advantage over indigenous bacteria.

Although indigenous bacteria are typically excellent competitors for forming root nodules, they are typically less efficient at nitrogen-fixation than inoculant bacteria. Therefore, in order for the inoculant bacteria to be capable of exerting their excellent nitrogen-fixing effects, they must first be able to out-compete the indigenous bacteria in order to form root nodules. Advantageously, the subject invention provides materials and methods which enable the inoculant bacteria to establish root nodules, even in the presence of indigenous bacteria.

In one aspect, the present invention provides isolated novel compounds which induce transcription of the nolA gene. These compounds are, collectively, referred to as nolA inducers. In soybean extracts, HPLC analysis of the compounds revealed at least two active compounds, referred to herein as IND-1 and IND-2. IND-1 has been identified as phthalic acid bis-(2-ethyl-hexyl) ester and is able to induce nolA . IND-1 has been identified as a contaminant of solvents used in the extraction process; however, phthalic acid bis-(2-ethyl-hexyl) ester is a potent inducer of nolA . IND-2 is a plant-produced NolA inducer that can be isolated according to the methods disclosed herein.

In addition to the plant-derived NolA inducers, the instant invention also provides isolated novel compounds produced by *B. japonicum* which induce nolA expression. These novel compounds may also be referred to as bacterial nolA inducers. The bacterial nolA inducer appears to be produced in a density dependent manner in batch culture and may be referred to as a "quorum sensing" molecule or cell density factor (CDF). Quorum sensing molecules regulate the expression of genes, such as nolA , in response to bacterial population density. The bacterial nolA inducer is insensitive to heat treatment and appears to have a molecular weight of less than 3,000 Da.

Compositions comprising one or more nolA inducers and a carrier are also taught according to the subject invention. NolA inducers include chemical compounds, plant-derived NolA inducers, and bacterial-derived NolA inducers. By way of example, compositions having a NolA inducer include commercially available soybean phosphatidyl inositol extracts, conditioned medium obtained from cultured *B. japonicum*, commercially available soybean extracts, or compositions having IND-1 (or isomers, analogs, or homologs thereof), IND-2, or CDF. The compositions may, optionally, include one or more NolA$^{INS}$ mutants.

Carriers useful in formulation of the compositions of the invention are well known to those skilled in the art and include those described in detail in a number of sources which are well known and readily available to those skilled in the art. Also contemplated as carriers are agricultural materials such as soil additives. Non-limiting examples of such additives include peat, soil conditioners, chemical fertilizers, and organic fertilizers (such as chicken or cow manure).

The present invention also provides bacterial cells which are insensitive to the effects of the nolA inducers. These bacterial cells are referred to as NolA$^{INS}$ mutants. An exemplary NolA$^{INS}$ mutant has been isolated and will be deposited with the American Type Tissue Culture [10801 University Blvd., Manassas, Va. 20110-2209].

Other NolA$^{INS}$ mutants include bacterial cells in which the gene or genes encoding the nolA inducer has been inactivated. Inactivation of the gene or genes encoding nolA inducers may be accomplished by deletion of all, or a portion, of the gene or genes encoding the nolA inducer, insertion of nucleic acid sequences within gene or genes encoding the nolA inducer or inactivation of transcriptional control sequences operably linked to nolA inducers. Alternatively, the nolA inducer gene may be inactivated by mutation or deletion of ribosome binding sites. Mutation or deletion of translation initiation sites may also be used to inactivate the nolA gene. Methods of site directed mutagenesis in Gram negative bacteria, such as Rhizobia, are well known to those skilled in the art.

NolA insensitive strains can be isolated using a variety of selection procedures. For example, since NolA inducers inhibit nodulation, one can select for NolA insensitive *B. japonicum* mutants by inoculating plants with a mutated population in the presence of the NolA inducer (e.g., IND-1, IND-2, or CDF, or quorum sensing factor). Bacteria isolated from nodules that form rapidly on the soybean roots would be presumptive mutants that were insensitive to the inhibitory effects of the nolA inducers. These mutants could then be confirmed by directly testing the ability of the inducers to activating transcription of nolA (e.g., using either Northern hybridization or measuring nolA-lacZ expression). Similarly, since nolA expression increases with culture age, plating of mutated *B. japonicum* cells (containing the nolA-lacZ fusion) on medium containing X-GAL (5-bromo-4-chloro-3- indolyl-β-D-galactoside) allows one to distinguish the blue, NolA expressing, and white, NolA non-expressing, cells. This system has been used to isolate and select mutants that are insensitive to the quorum sensing inducer that is expressed in the colonies after prolonged growth (i.e., cells remaining white).

This same selection scheme can also be used to isolate *B. japonicum* mutants that lack the ability to produce quorum sensing factor. These mutants should also appear white after prolonged growth. These mutants can also be selected by plating a mutated population of *B. japonicum* and then overlaying these colonies with soft agar (0.4%) containing a *B. japonicum* strain with the nolA-lacZ fusion and X-GAL. Mutants defective in production of the quorum sensing factor will not induce the nolA-lacZ fusion in the overlay, while those still producing the factor will rapidly induce the fusion resulting in a blue color.

The subject invention advantageously provides methods of increasing nitrogen fixation in plants by applying a nodulation inoculant having NolA$^{INS}$ mutants and one or more nolA inducers to plants. In a preferred embodiment, the plants are legumes; in a more preferred embodiment, the plants are soybeans. The inoculant contains NolA$^{INS}$ mutants in amounts effective to induce nodulation in the plant and amounts of one or more nolA inducers sufficient to induce the activity of the nolA gene. Methods of preparing inoculants, or coating seeds with inoculants, suitable for use in the present invention are well known in the art and include those taught in U.S. Pat. Nos. 4,535,061, 5,173,424, 5,695, 541, and 5,916,029 hereby incorporated by reference in their entireties.

The subject invention also provides methods of producing a nodulation inoculant containing reduced amounts of quorum factor (CDF). These improved nodulation inoculants are produced by adding iron to cultures containing nodulating bacterial cells. As used herein, a nodulation inoculant includes any bacterial species that nodulates a plants. Nodulation inoculants produced according to these methods contain lower amounts of quorum factor (CDF) as compared to nodulation inoculants not grown in the presence of iron, and are able to more efficiently nodulate target plant species (as compared to indigenous nodulating bacterial cells or nodulation inoculants not grown in the presence of iron).

The subject invention further provides methods of reducing the production of cell density factor or quorum factor in a nodulation inoculant or a method of increasing the nodulation efficiency of a nodulation inoculant comprising the addition of iron to medium containing the nodulation inoculant. Iron is added in amounts sufficient to suppress the production of cell density factor or quorum factor.

In some embodiments of the above-identified methods, the iron is in the form of compounds containing $Fe^{3+}$. One embodiment provides iron in the form of $FeCl_3$. As would be apparent to one skilled in the art, nodulation inoculants can be prepared by culturing the bacterial cells in any size container. For example, the cells can be cultured in a fermenter, batch cultured, cultured on solid medium, cultured in standard culture flasks, or cultured in test tubes.

In various embodiments, iron is added to the culture medium at various stages of bacterial growth in amounts sufficient to suppress the production of CDF or quorum factor. Thus, iron can be added to nodulation inoculants in lag, early exponential, exponential, late exponential, early stationary, or stationary growth phase. In other embodiments, the iron can be added to the culture medium prior to the addition of an inoculant starter culture; alternatively, iron can be added to the starter culture and this admixture then added to the culture medium. Iron can also be added to the culture medium and the starter culture. Various embodiments of the invention provide for the addition of at least about 0.05 μM or at least about 0.1 μM of iron. Other embodiments provide for the addition of iron in concentrations of at least about 1 μM, 10 μM, 100 μM, or at least about 1 mM. Iron concentrations that ranges from 0.5

μM to 1M can be also be used in the practice of the instant invention. In some embodiments, the iron has a concentration that ranges from 1 μM to 500 mM. Other embodiments provide iron concentrations that range from 10 μM to 250 mM or from 100 μM to 100 mM. Alternatively, iron can be added in a range of 500 μM to 50 mM, 750 μM to 5 mM, or about 1 mM. Each of these ranges is to be construed as providing written support of an iron concentration ranges falling within the range. For example, the range of 100 μM to 100 mM is also to be construed as providing written support for a ranges such as 300 μM to 50 mM, 400 μM to 10 mM, or 500 μM to 1 mM. Furthermore, as would be apparent to the skilled artisan, aseptic or sterile techniques can be utilized in the practice of the invention.

In some embodiments, the nodulation inoculant comprises a single species or strain of nodulating bacteria. Other embodiments provide for the combination of different species of nodulating bacteria. Thus, combination of at least two different species of nodulating bacteria can be used in the practice of the disclosed inventions. In some embodiments, the nodulating bacteria is one or more species or strain of Bradyrhizobium. Other non-limiting examples of inoculants that can be produced according to the instant invention include *Parasponia rhizobium* (now identified as *B. parasponia*), *Rhizobium leguminosarum* biovars *viciae, trifolii* and *phaseoli, Rhizobium* sp. NGR234, *B. japonicum* USDA 110 and 123, *Rhizobium etli, Sinorhizobium meliloti, Rhizobium leguminosarum* spp., or those listed in FIGS. 17–18.

The subject invention also provides for methods of screening organisms or extracts for the production of IND-1, IND-2, CDF (quorum factor), or CDF-like molecules. In this method, extracts or culture supernatants are analyzed for their ability to modulate nolA-lacZ, nodY-lacZ, nodC-lacZ, or nodD-lacZ fusions in transformed host cells. For example, where such molecules are present in the extract or supernatant, nolA expression is induced. In contrast, very little induction is observed with samples where no IND-1, IND-2, CDF (quorum factor), or CDF-like molecules are present. Conditioned medium from organisms to be tested for the presence of CDF or CDF-like molecules can also be used in the subject screening methods.

A further aspect of the subject invention relates to polynucleotides encoding nolA inducers of the subject invention. The polynucleotide sequence encoding the nolA inducers may, optionally, be operably linked to transcriptional control sequences. As is apparent to one of ordinary skill in the art, the disclosed inducers may be encoded by multiple polynucleotide sequences because of the redundancy of the genetic code. It is well within the skill of a person trained in the art to create these alternative DNA sequences encoding the same, or essentially the same, proteins. As used herein, reference to "essentially the same" sequence refers to sequences which have amino acid substitutions, deletions, additions, or insertions which do not materially affect biological activity of the inducers of the invention (namely the ability to induce nolA). Fragments of the inducers which retain the ability to induce nolA expression are also included in this definition.

The polynucleotides of the subject invention include vectors and expression cassettes. The vectors and expression cassettes may contain transcriptional control sequences which are operably linked to polynucleotide sequences encoding the nolA inducers of the instant invention. The vectors and expression cassettes of the invention may further include selectable markers.

The subject invention also provides transformed plant cells and transgenic plants which have one or more polynucleotide sequences which encode plant-derived or bacterial-derived nolA inducers. The polynucleotide sequences encode compounds which induce the expression of nolA, thereby reducing nodulation in plants by susceptible bacteria. Methods of transforming cells with polynucleotide sequences, vectors, or expression cassettes which encode nolA are well known to those skilled in the art. Plants and plant cells may be transformed by, for example, electroporation, Agrobacterium transformation, engineered plant virus replicons, electrophoresis, microinjection, microprojectile bombardment, micro-LASER beam-induced perforation of cell wall, or simply by incubation with or without polyethylene glycol (PEG).

The method of increasing nitrogen fixation in plants, to which the NolA$^{INS}$ mutants are applied, may be practiced in transgenic plants which express the nolA inducer and non-transgenic plants which constitutively express the nolA inducer; this method may involve the application of compositions having NolA$^{INS}$ mutants (bacterial cells) directly to the roots of transgenic plants having polynucleotides encoding a nolA inducer. The compositions having NOlA$^{INS}$ mutants may, optionally, further include one or more nolA inducers. In one embodiment, the roots may be wounded to enable the NolA$^{INS}$ bacterial cells to penetrate the roots more quickly and easily; however, wounding of the roots is not required. In a preferred embodiment, the plants are legumes. More preferably, the plants are soybeans.

The present invention also provides methods of reducing or inhibiting the nodulation activity of indigenous *B. japonicum* by adding a composition having one or more nolA inducers of the invention to soil. In this aspect of the invention, NolA$^{INS}$ bacterial cells may, optionally, be included in the composition. The soil to which these compositions are added include active and fallow fields.

To facilitate understanding of the invention, a number of terms are defined below. All publications, patents and patent applications cited herein, whether supra or infra, are hereby incorporated by reference in their entirety to the extent that the reference is not inconsistent with the teachings provided herein. As used in this specification and the appended claims, the singular forms "a," "an" and "the" include plural references unless the context clearly dictates otherwise.

As used herein, the term "transgenic plants" refers to plants (monocots or dicots), having plant cells in which heterologous polynucleotides, such as those encoding plant or bacterial nolA inducers, are expressed as the result of manipulation by the hand of man.

As used herein, the term "peptide" refers to a polymer of amino acids and does not refer to a specific-length of the product; thus, polypeptides, oligopeptides, and proteins are included within the definition of peptide. This term also does not refer to, or exclude, post expression modifications of the peptide, for example, glycosylations, acetylations, phosphorylations and the like. Included within the definition are, for example, peptides containing one or more analogs of an amino acid (including, for example, unnatural amino acids, etc.), polypeptides with substituted linkages, as well as other modifications known in the art, both naturally occurring and non-naturally occurring.

The terms "purified" and "isolated" indicate that the molecule is present in the substantial absence of other molecules of the same type. The term "purified" as used herein preferably means at least 75% by weight, more preferably at least 85% by weight, more preferably still at least 95% by weight, and most preferably at least 98% by weight, of molecules of the same type are present.

The terms "purified" and "isolated", when referring to a polynucleotide, nucleotide, or nucleic acid, indicate a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecules but is not flanked by both of the coding or non-coding sequences that flank that part of the molecule in the genome of the organism in which it naturally occurs (e.g., DNA excised with a restriction enzyme); (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library.

The term "polynucleotide" as used herein refers to a polymeric form of nucleotides of any length, either ribonucleotides or deoxyribonucleotides. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications, such as those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

By "vector" is meant any genetic element, such as a plasmid, phage, transposon, cosmid, chromosome, virus etc., which is capable of replication when associated with the proper control elements and which can transfer gene sequences between cells. Thus, the term includes cloning and expression vehicles, as well as viral vectors.

In order to provide a means of selecting transformed plant or bacterial cells, the vectors for transformation will typically contain a selectable marker gene. Marker genes are expressible DNA sequences which express a polypeptide which resists a natural inhibition by, attenuates, or inactivates a selective substance. Examples of such substances include antibiotics and, in the case of plant cells, herbicides. Suitable marker genes for use in this invention are well known to those skilled in the art.

It is also contemplated that a particular amino acid sequence of NolA may be encoded by more than one polynucleotide sequence. It may be advantageous to produce nucleotide sequences possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence without altering the encoded amino acid sequence include the production of RNA transcripts having more desirable properties, such as a longer half-life, than transcripts produced from the naturally occurring sequence.

MATERIALS AND METHODS

Bacterial Stains, plasmids and culture conditions. For routine bacterial growth, *B. japonicum* cells were maintained on RDY medium (So, J. -S. et al. [1987] *Mol. Gen. Genet.* 207:15–23). Bacteria were grown in minimal medium (Bergensen, F. J. [1961] *Aust. J. Biol. Sci.* 14:349–360) for β-galactosidase activity. As required, antibiotics were used at the following concentrations, Cm (30 µg/ml), Sm (100 µg/ml), Sp (100 µg/ml), Tc (100 µg/ml). The *B. japonicum* strains used in this study were Bj110-42, BJAlac12, BJAlac23, BJAlac13 and BJ110-1248-1, ZB977, SL101 and Bj110-573. These strains harbored the following translational fusions; BJ110-1248-1 (nodD$_2$-lacZ, plasmid pRJ1248, Dockendorff et al. [1994] *Mol. Plant-Microbe Interact.* 7:596–602), ZB977 (nodY-lacZ, plasmid pZB32, Banfalvi et al. [1988] *Mol. Gen. Genet.* 214:420–424), SL101 (npt-lacZ, Yuen, J. P.-Y and G. Stacey [1996] *Mol. Plant-Microbe Interact.* 9:424–428), and Bj110-573 (nodC-lacZ, chromosomally integrated fusion, Dockendorff et al. [1994] *Mol. Plant-Microbe Interact* 7:596–602). Strains Bj110–42, BJAlac23, BJAlac12, BJAlac13 harbored nolA-lacZ translational fusions encoded on plasmids pBGALac1, pNMAlac23, pNMAlac13, pNMAlac12 respectively (Garcia et al. [1996] *Mol. Plant-Microbe Interact.* 9:625–635; Loh et al. [1999] *J. Bacteriol.* 181:1544–1554). Plasmid pNMAlac23 contained mutations to ATG2 and ATG3 of nolA and allowed the specific expression of NolA$_1$-lacZ. In contrast, plasmids pNMAlac13 (mutations to ATG1 and ATG3) and pNMAlac12 (mutation to ATG1 and ATG3, Loh et al. [1999] *J. Bacteriol.* 181:1544–1554) only expressed NolA$_2$-lacZ and NolA$_3$-lacZ, respectively.

Following are examples which illustrate procedures for practicing the invention. These examples should not be construed as limiting. All percentages are by weight and all solvent mixture proportions are by volume unless otherwise noted. All references, publications, and patents cited herein are hereby incorporated by reference in their entireties.

EXAMPLE 1

Identification of NolA Inducers from Plant Extracts

While many of the nodulation genes of *B. japonicum* are induced by the plant flavonoids genistein and daidzein, these compounds and a variety of other flavonoids failed to induced nolA expression. NolA expression was, however, induced by plant extracts. Analysis of these extracts, using Reverse Phase HPLC, have identified the presence of two distinct compounds (IND-1 and IND-2) that are capable of inducing nolA (FIG. 1).

Figure 2A:
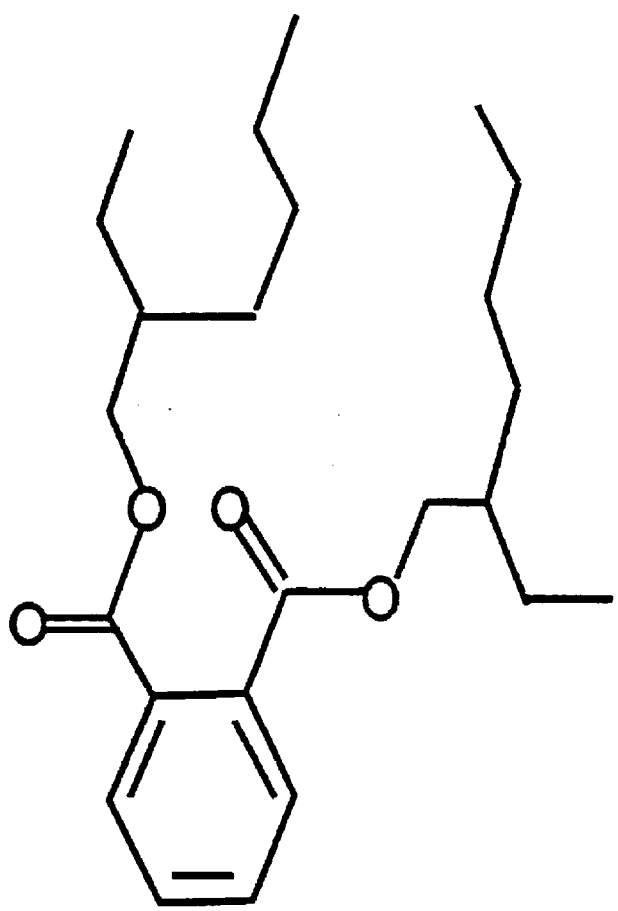
Figure 2B:
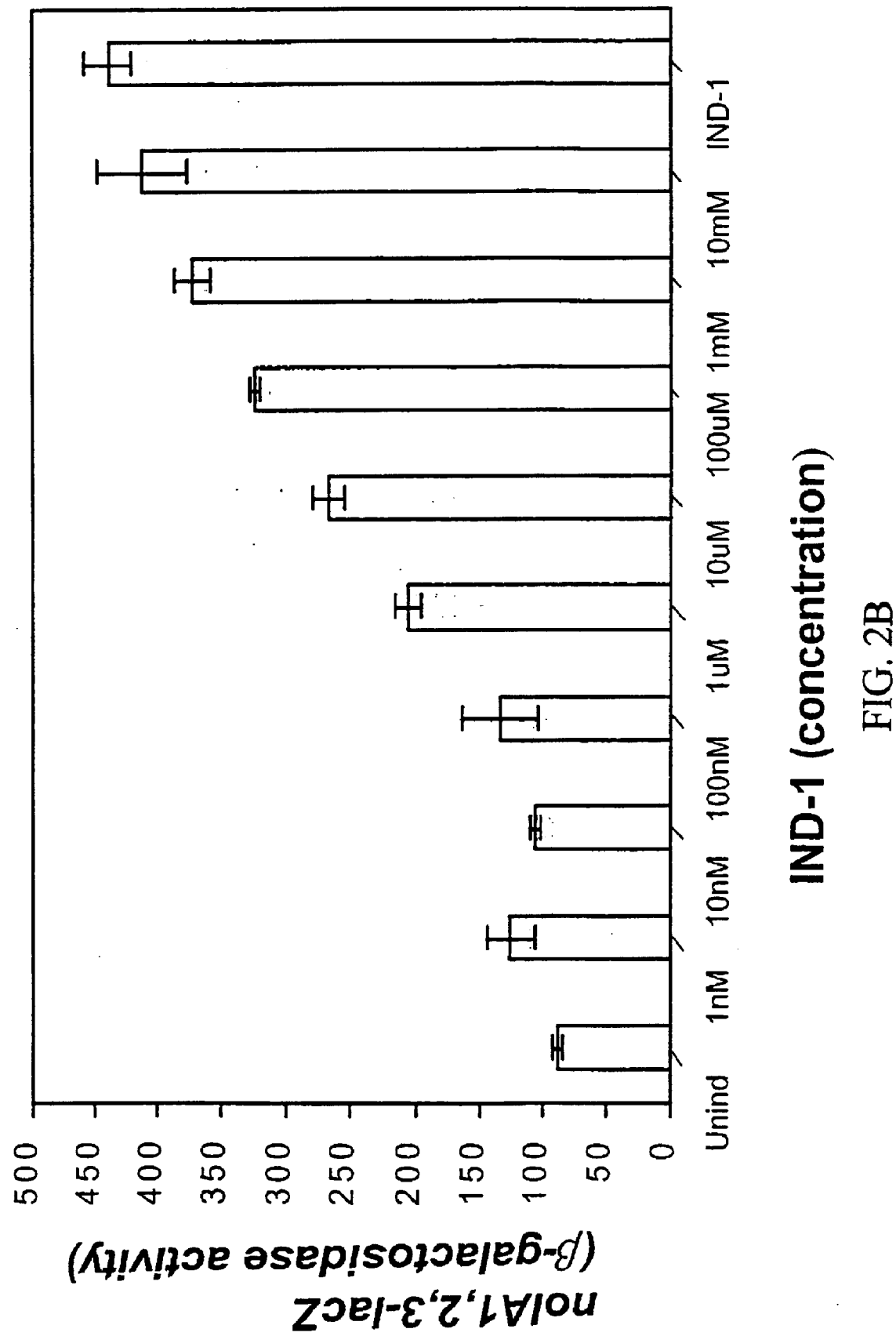

IND-1 has been identified as a phthalic acid bis-(2-ethyl-hexyl) ester (FIG. 2A). To confirm the activity of this compound, phthalic acid bis-(2-ethyl-hexyl) ester was chemically synthesized and shown to be able of inducing nolA expression (FIG. 2B). This compound is a strong inducer of NolA expression and inhibits nodulation.

Figure 3:
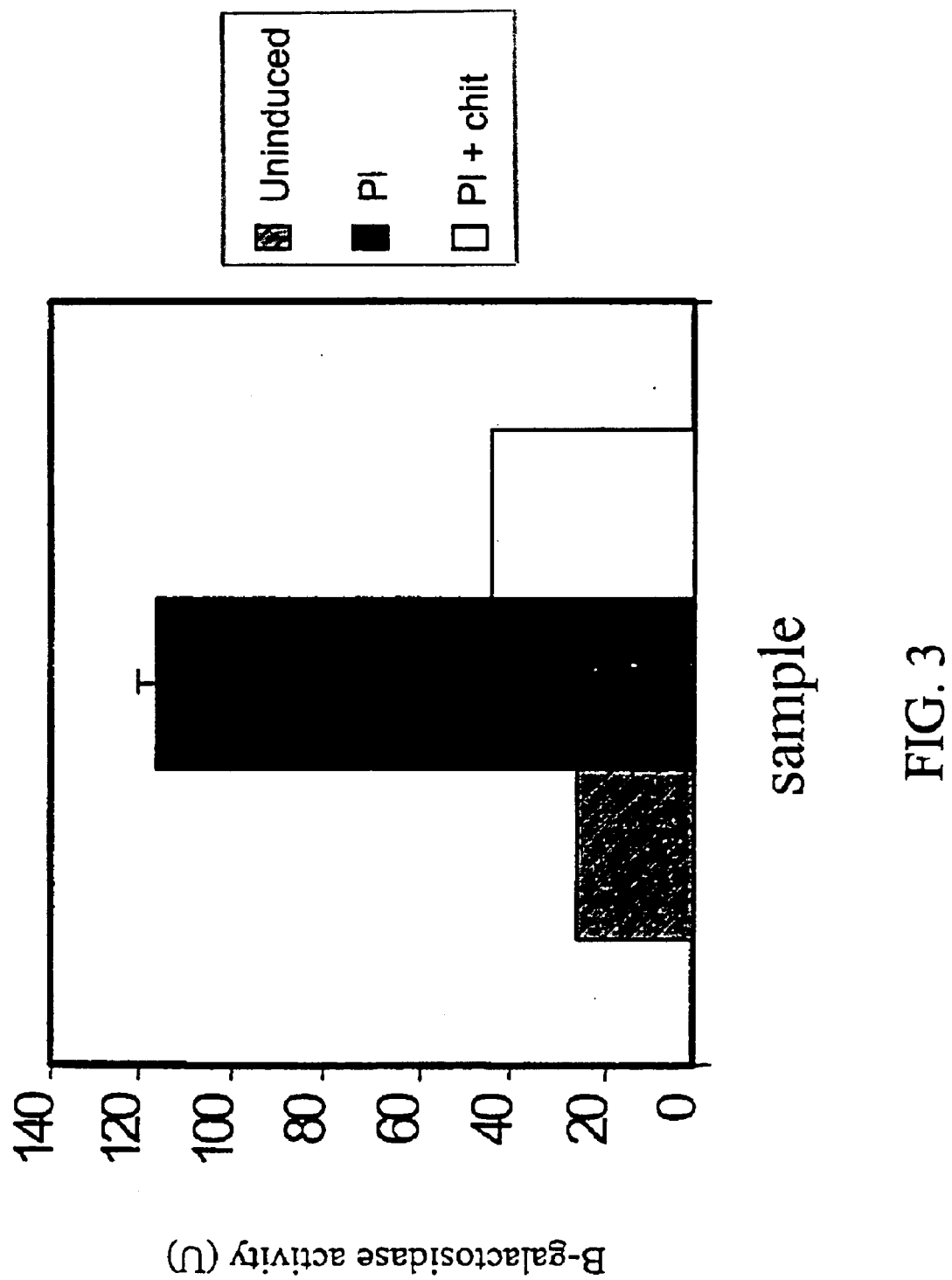
Figure 4A:
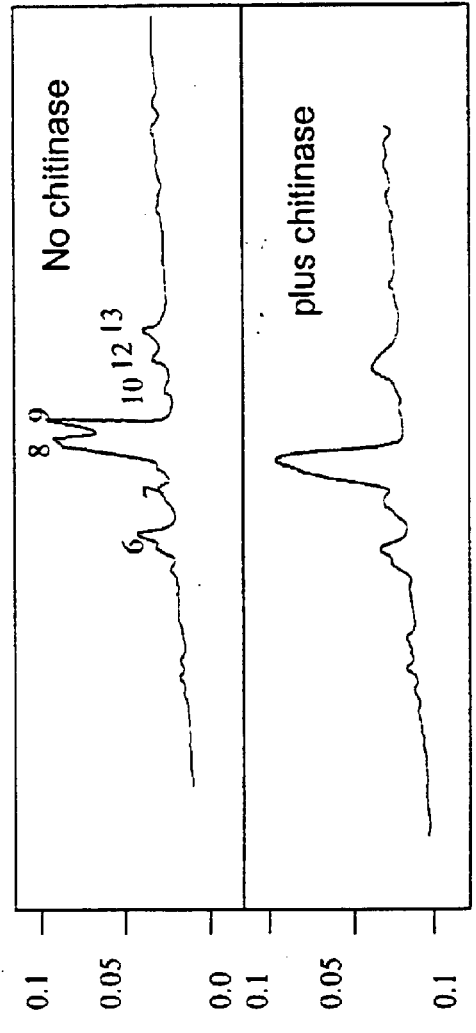
Figure 4B:
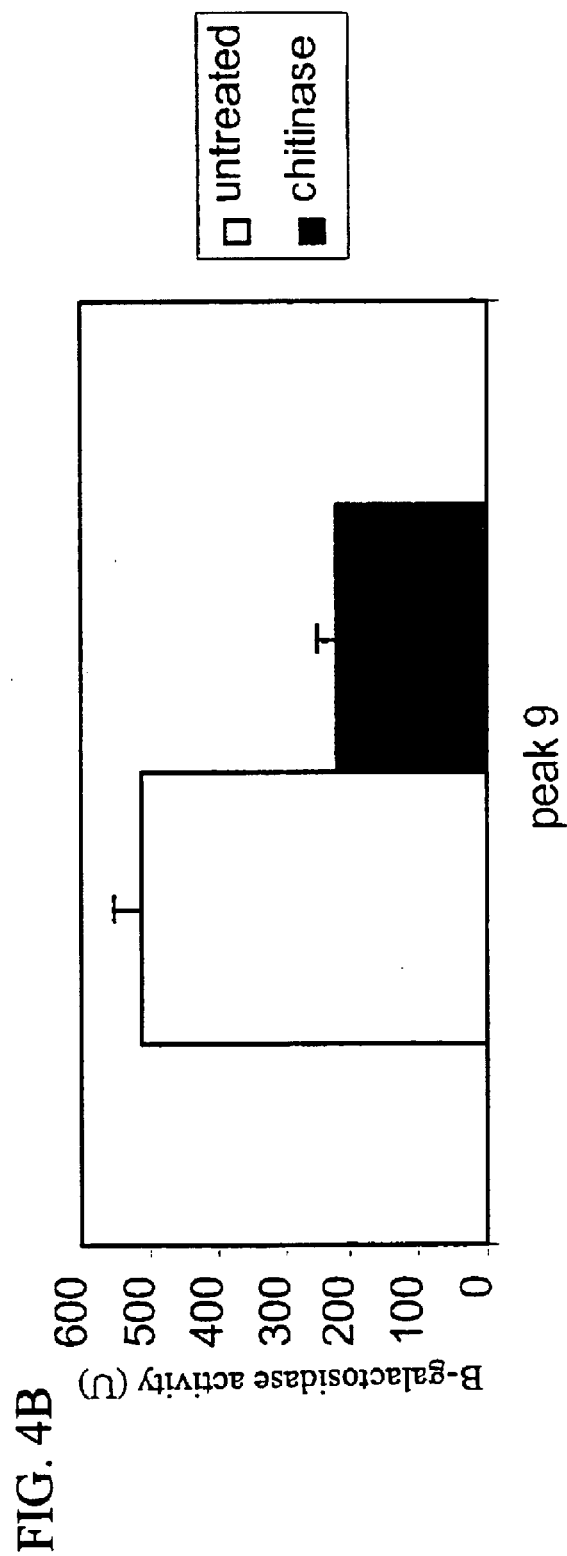

Initial analysis of IND-2 indicates that its activity is sensitive to chitinase treatment. IND-2 may also be purified from soybean extracts, particularly commercially available soybean phosphatidylinositol extracts (available from companies such as Sigma Chemical Co., St. Louis, Mo.). When tested, the commercially available phosphatidylinositol soybean extracts (Sigma) were found to be capable of inducing nolA expression (FIG. 3). Moreover, these extracts were also sensitive to chitinase treatment. As shown in FIGS. 4A–4B, we have identified a peak (i.e. peak 9) after Reverse Phase HPLC, that is both capable of inducing nolA and sensitive to chitinase. Materials containing IND-1 and IND-2 were applied to a C18 column (Phenomenex, Inc., Torrance, Calif.) and eluted with a methanol gradient (0–100%) at a flow rate of 1 mL per minute.

EXAMPLE 2

NolA Inducer from *B. japonicum*

Typically, *B. japonicum* cells are found in high population density in commercial inoculants. To determine if the bacterial nolA inducer was present in commercial inoculant, three soybean inoculants from two commercially available sources were extracted with butanol, and these extracts analyzed for their ability to induce the nolA-lacZ fusions. As shown in Table 1, nolA expression was induced significantly by the *B. japonicum* inoculant extracts. In contrast, very little induction was observed with samples where no *B. japonicum* were present (i.e., peat alone).

EXAMPLE 3

Quorum Control Mechanism for NolA Induction

Figure 5A:
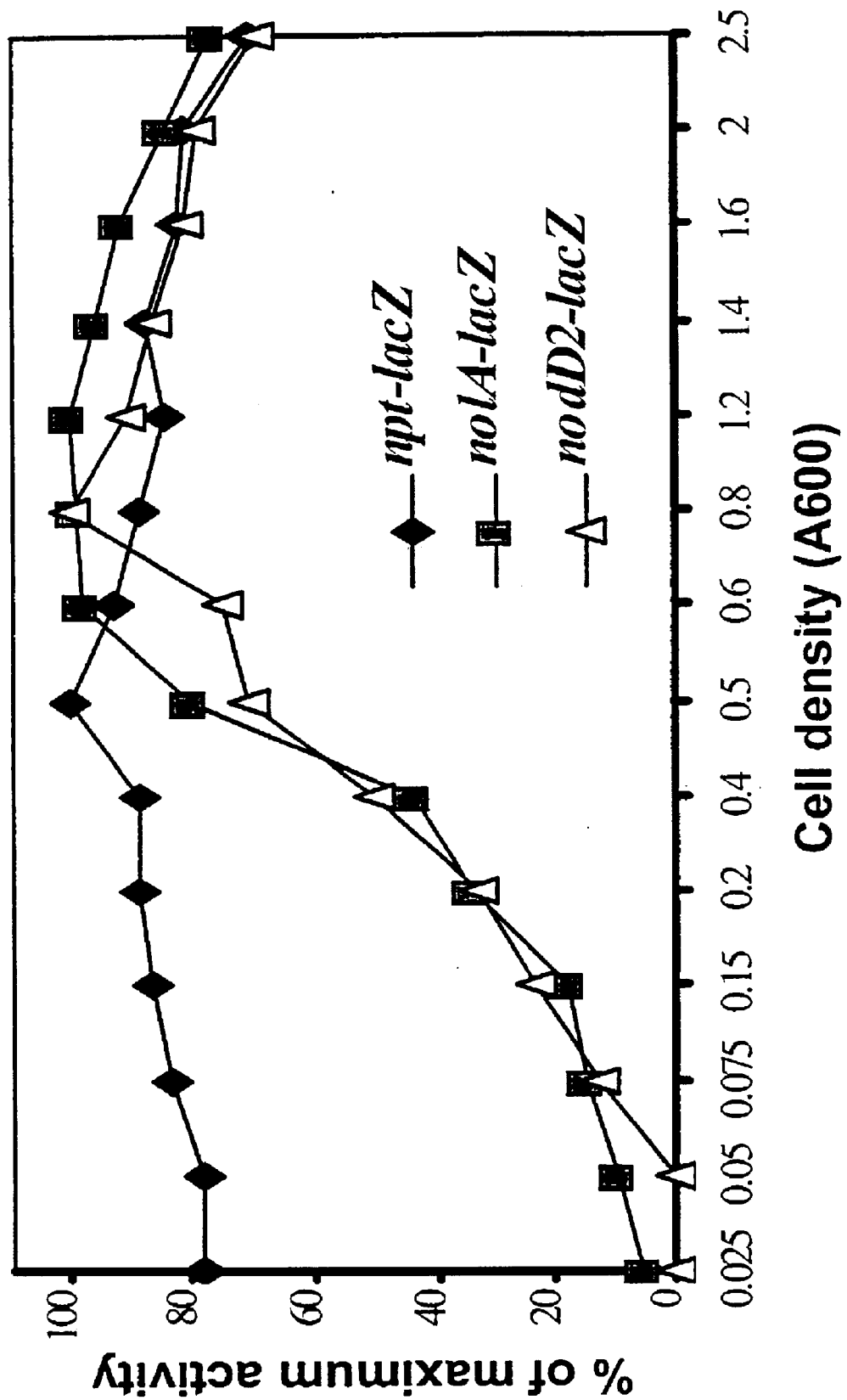
Figure 5B:
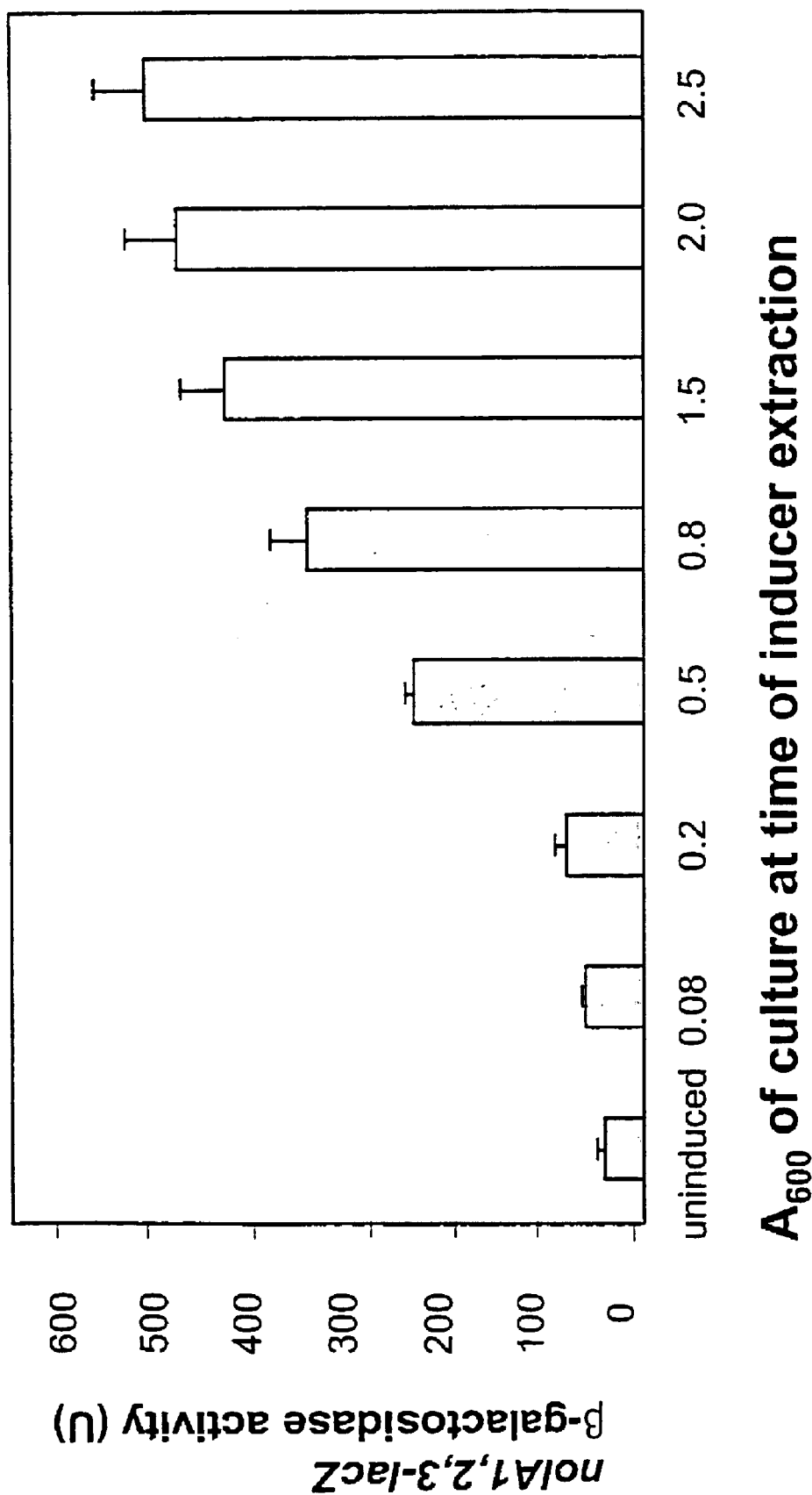

NolA expression is population density dependent; its expression is low at a low population density, and significantly higher in more dense cultures (FIG. 5). This quorum control of nolA expression appears to be regulated by a compound that is secreted and accumulates in the culture medium. Addition of this compound (i.e. conditioned medium) to *B. japonicum* cultures grown to a low population density greatly increases the expression of nolA (Table 2). Consistent with the fact that nolA regulates $nodD_2$, the levels of $nodD_2$ expression not only showed a similar population density dependence (FIG. 6, Table 2), but were also found to be affected by the addition of the nolA inducer.

Figure 11A:
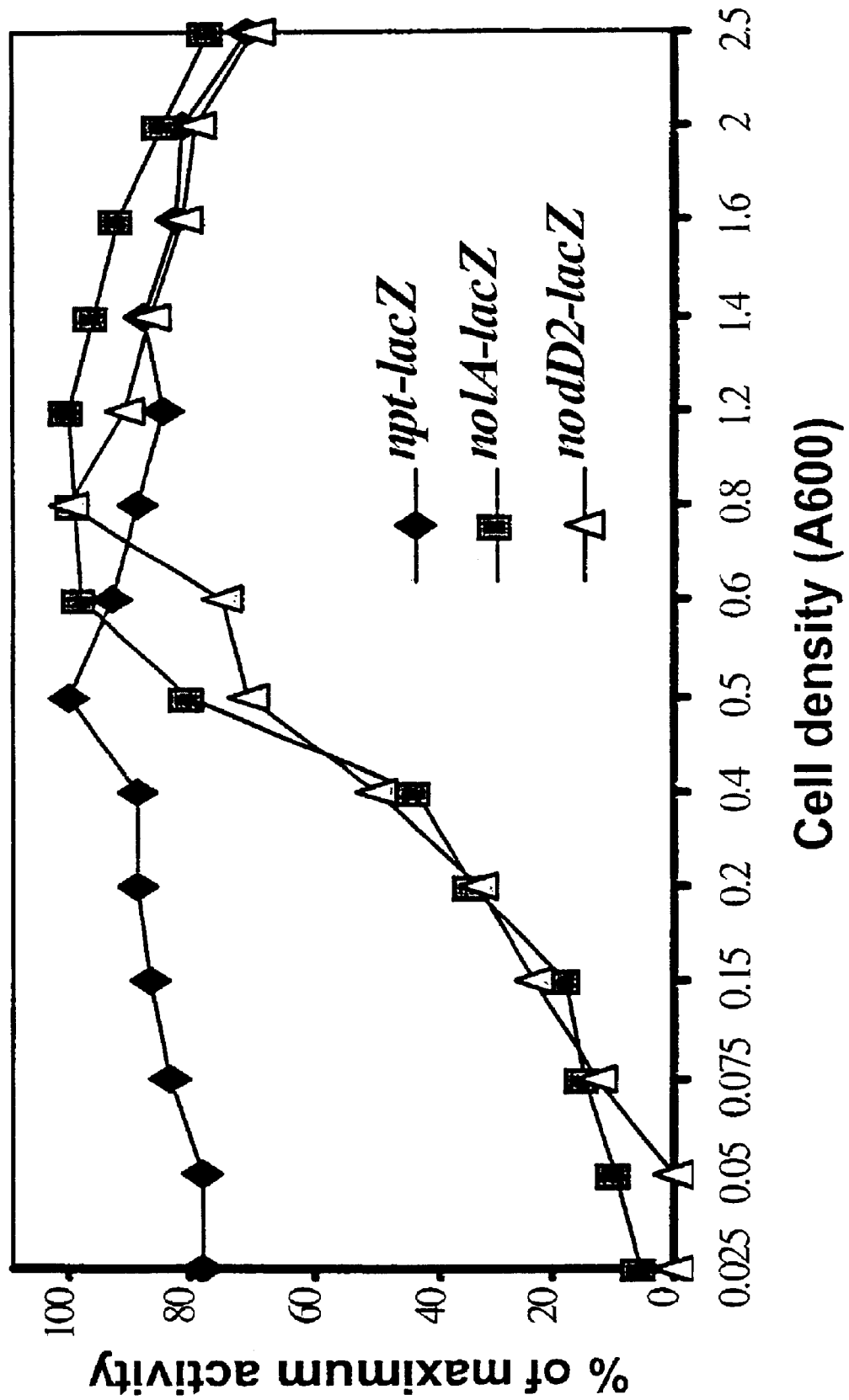
Figure 11B:
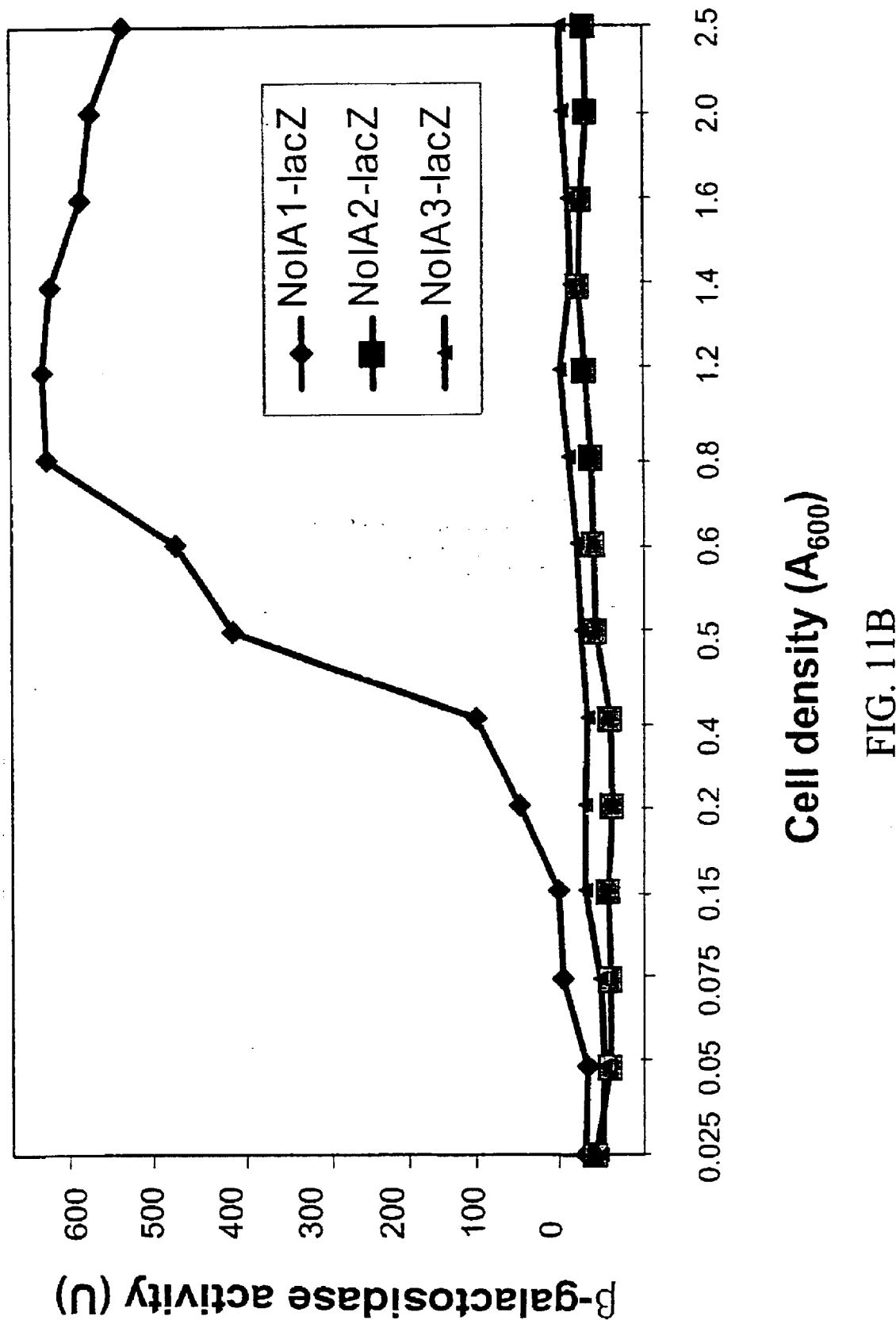
Figure 11C:
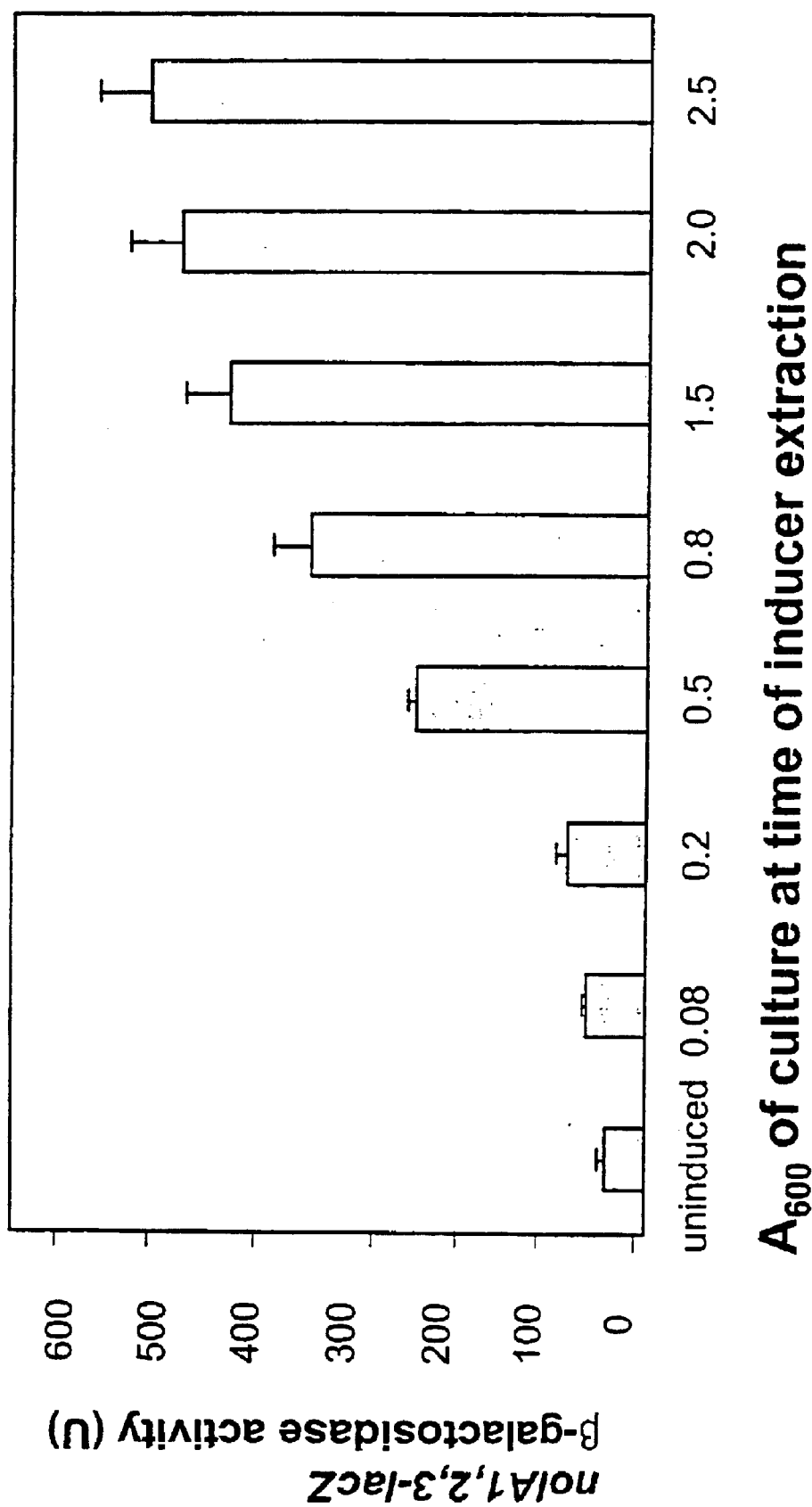

As shown in Tables 2–3 and FIG. 11C, an inducer of nolA-lacZ and $nodD_2$-lacZ expression was detected in conditioned medium from *B. japonicum* cultures grown to a high population density. This inducer was capable of inducing transcription of both fusions when added to *B. japonicum* cultures at 10 µl/ml. The ability of the conditioned medium to induce the nolA fusions was population density dependent with little or no induction of the fusions observed using conditioned medium derived from cultures of $A_{600}$<0.2 (FIG. 11C). Significant induction was observed with conditioned medium from cultures of $A_{600}$=0.5, reaching a maximum at $A_{600}$>1.0. The bacterially derived inducer within the conditioned medium is insensitive to heat. The nolA inducer present in the conditioned medium was lost after dialysis using a membrane with a cutoff at 3 kDa (Fisher Scientific, Pittsburgh, Pa.).

EXAMPLE 4

Population Density Dependence of Nod Gene Expression

Figure 6:
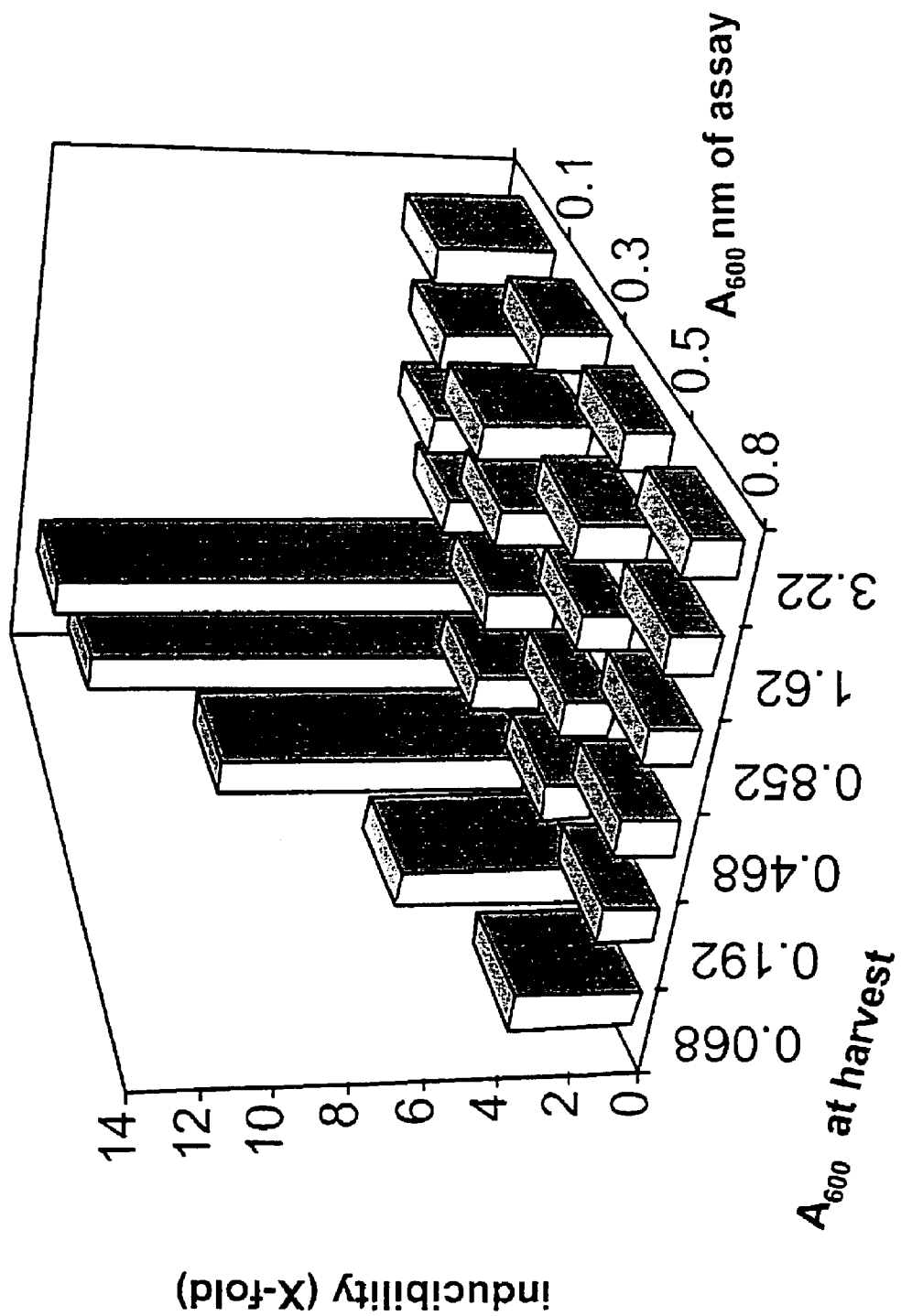

Nod gene induction by genistein is population-density dependent. It has been observed that optimal gene expression occurs at very low population densities (i.e., $A_{600}$<0.05, Yuen, J. P.-Y. and G. Stacey [1996] *Mol. Plant-Microbe Interact.* 9:424–428). In order to examine this observation in a systematic way, Bj110-573 cells (containing a chromosomally integrated nodC-lacZ fusion, Dockendorff, T. C. et al. [1994] *Mol. Plant-Microbe Interact.* 7:596–602) were cultured to various population densities. Aliquots were taken from these cultures, adjusted to specific, initial population densities, and tested for nodC-lacZ induction using a sub-optimal level of genistein (0.025 µM). In each of these experiments, cells were cultured in the presence of the inducer for 5 hours; a time period that previous experiments had indicated resulted in optimal nodC-lacZ expression. This experimental design allowed for the analysis of nodC-lacZ expression as a function both of the inoculum population density and the initial population density of the inducer-treated aliquots. As shown in FIG. 6, the inducibility of nod gene expression was highest in samples where the inoculum cultures were grown to low optical population densities. For example, an inoculum culture grown to an $A_{600}$=0.068 was significantly more inducible than a culture grown to an $A_{600}$=0.852 regardless of the density at which these cells were assayed. Little or no nodC induction was observed with cells harvested at high population densities (e.g., $A_{600}$=1.62 or 3.22).

A similar dependence on population density was also observed when the levels of nod gene expression were examined relative to the density of the cell suspension treated with inducer. For example, cells harvested at an $A_{600}$=0.192 showed very high levels of nodC-lacZ expression when induced at an $A_{600}$=0.1 but inducibility was markedly reduced when the same cells were assayed at an $A_{600}$=0.3. These results support the notion that the responsiveness of *B. japonicum* cells to the nod gene inducer, genistein, is affected by culture age, but is more directly related to culture population density.

EXAMPLE 5

Figure 7:
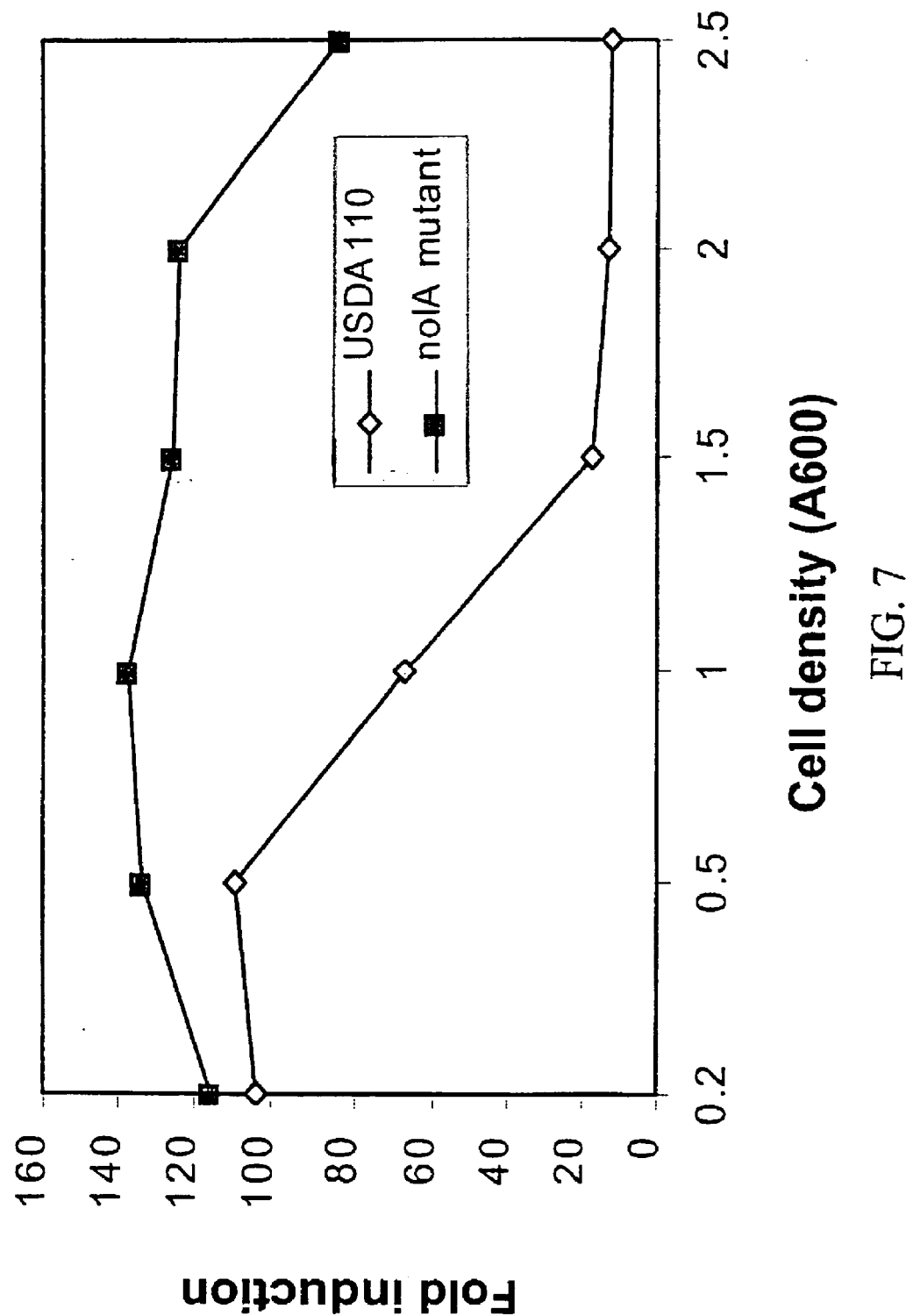

Nod Gene Expression nodY-lacZ induction by genistein was highest at a low population density and drastically reduced at high cell cultures. The fact that nolA is involved in the negative regulation of the nod genes and that its expression increased in cultures of higher population density, suggested a role for this protein in population density dependent nod gene repression. This view is supported experimentally by the following two results. First, nodY-lacZ expression in a nolA mutant was found to be unaffected by population density (FIG. 7). Moreover, when the population density dependent factor was added to *B. japonicum* cultures grown to a low population density, the levels of nod gene induction by isoflavonoids were significantly reduced (Table 2). It is, therefore, likely that high population densities coupled with increased nolA expression in response to a bacterial quorum factor leads to elevated expression of the repressor $NodD_2$; this results in negative control of the flavonoid inducible nod genes.

EXAMPLE 6

Effect of IND-1 on nod Gene Expression

Figure 8:
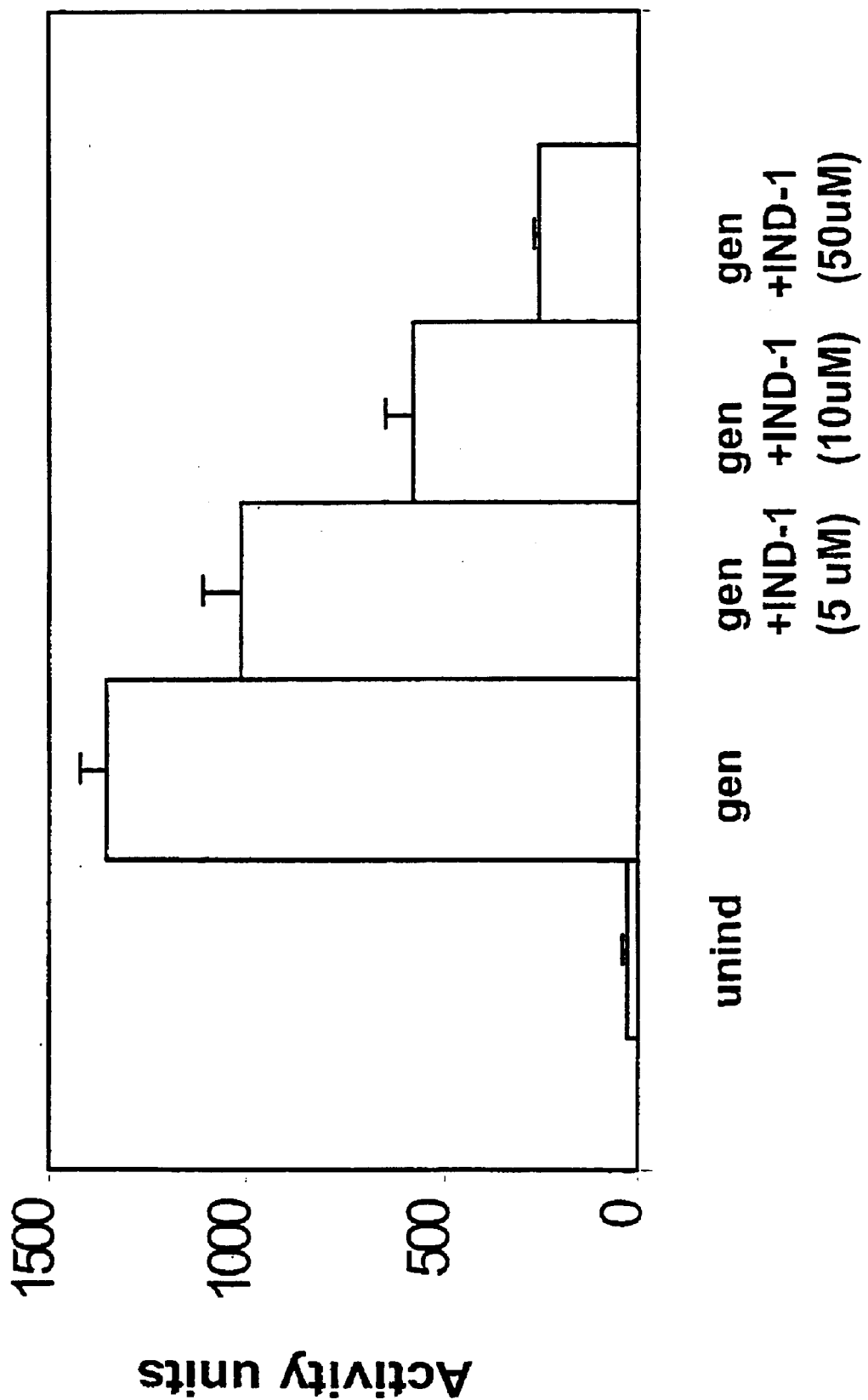
Figure 9:
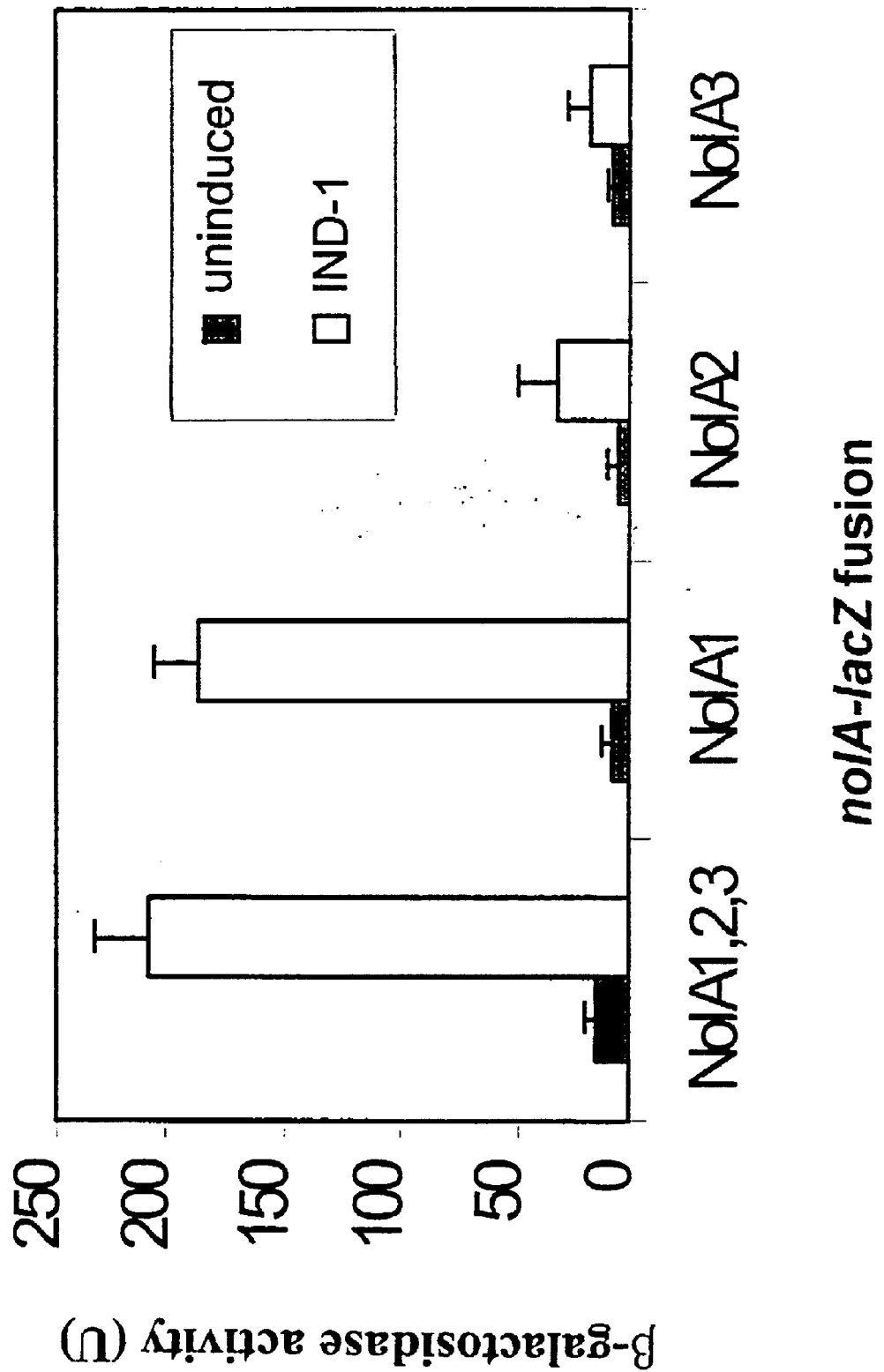

The levels of nod gene expression were also found to be affected by IND-1. Similar to the bacterial factor, incubation of IND-1 with *B. japonicum* cells reduced nodY-lacZ induction by genistein (FIG. 8). This inhibition was observed in three *B. japonicum* strains tested (i.e., USDA110, USDA76, USDA31), suggesting a general effect of nod gene repression by IND-1. When further analyzed, we noted that both the quorum factor and IND-1 appeared to affect only $NolA_1$ expression, but not $NolA_2$ or $NolA_3$ (Table 2, FIG. 9).

EXAMPLE 7

Effect of IND-1 and Quorum Factor on Nodulation

The significance of nod gene repression by both IND-1 and the quorum factor was also investigated in plant tests. Seeds of *Glycine max*cv *Essex* were surface sterilized, placed in sterile growth pouches (Mega International, MN) and cultivated as described by Nieuwkoop et al. (Nieuwkoop et al. [1987] *J. Bacteriol.* 169:2631–2638). Each seedling was inoculated with $10^7$ *B. japonicum* cells. Prior to inoculation of the roots, *B. japonicum* cells were incubated for 1 h with concentrated, conditioned medium that had been sterilized by filtration through a 0.45 µM filter (Millipore, Bedford, Mass.). The conditioned medium was used at a final concentration of 10 µl per 1 ml of culture. At the time of inoculation, the location of the root tip was marked on the outside of the plastic growth pouch. Plants were watered with nitrogen free nutrient solution (Wacek and Brill [1976] *Crop Sci.* 15:519–523). At 21 days post-inoculation, the number of nodules on each root both above and below the root tip mark was recorded.

Figure 10:
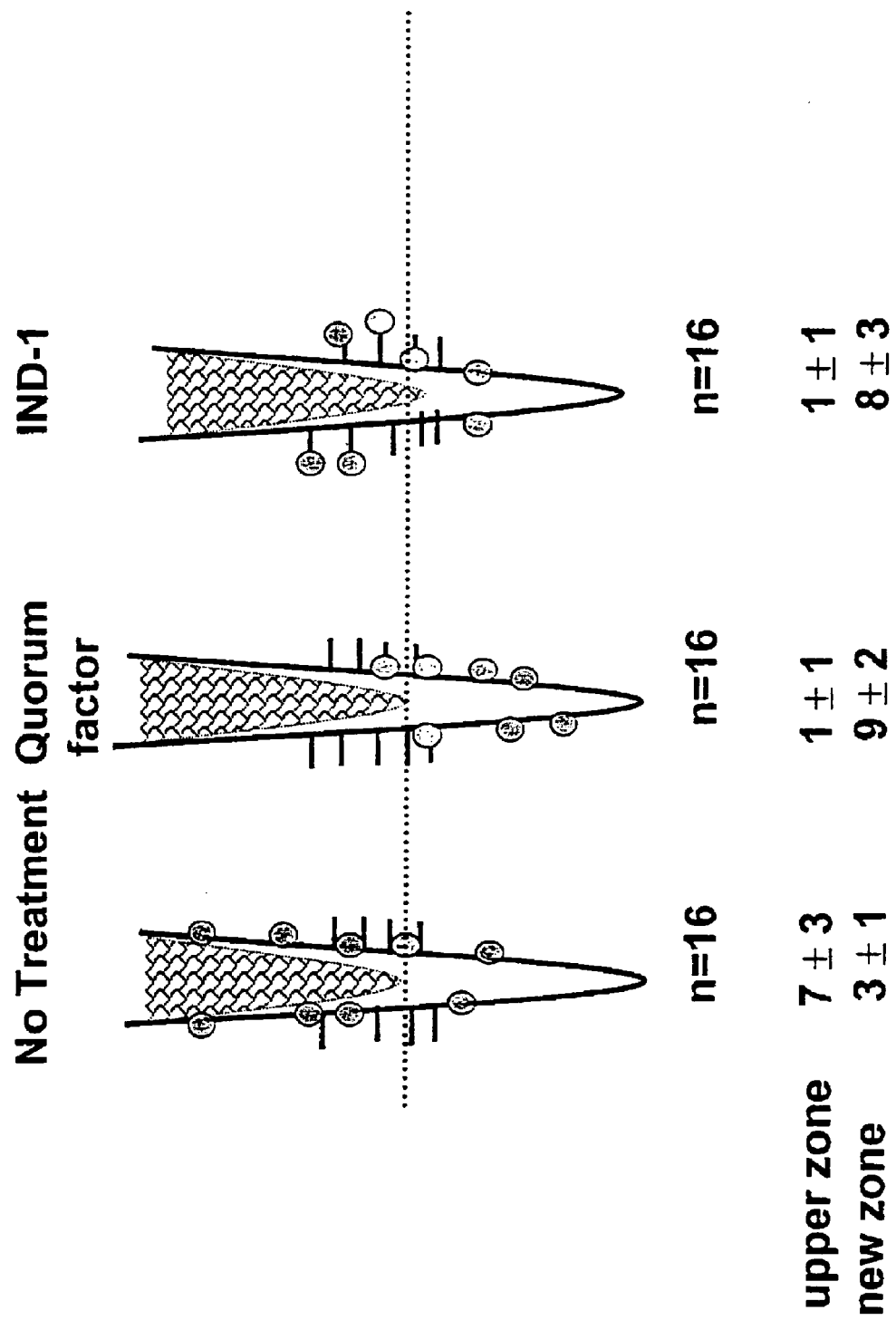

Consistent with the fact that the nodulation genes are critical for effective nodulation, pretreatment of *B. japonicum* cells with either IND-1 or the quorum factor resulted in reduced nodulation efficiency. This is shown in FIG. 10, where a delay in nodulation in both IND-1 and quorum factor treated samples, is reflected by an increased number of nodules on both lateral roots as well as below the RT mark (i.e. root tip mark at the time of inoculation).

Such a delay in nodulation is significant in light of results presented above that demonstrate that the quorum determinant is also present in commercial preparations used as soybean inoculants. In these inoculants, the levels of quorum factor would be present in sufficient levels to repress any stimulation of the nod genes by plant produced isoflavonoids, thereby reducing the ability of *B. japonicum* in these inoculants to nodulate the soybean plant.

EXAMPLE 8

Cell Population Density Dependence of NolA Expression

The expression of $nodD_2$-lacZ and nolA-lacZ fusions as a function of *B. japonicum* culture density was examined (FIG. 11A). Both nolA-lacZ and $nodD_2$-lacZ expression exhibited a basal level of transcription until mid-log phase ($A_{600}$=0.5) at which time expression increased to a maximum at a population density of $A_{600}$>1.0. The level of $nodD_2$-lacZ expression in the NolA mutant strain BjB3 (Garcia et al. [1996] *Mol. Plant-Microbe Interact.* 9:625–635) did not increase with population density and remained at background levels throughout the experiment (data not shown). Thus, these data indicate that the level of NolA expression increases with population density resulting in an elevated level of $NodD_2$ production. As a control, the level of neomycin phosphotransferase (npt-lacZ) production was not affected by population density indicating that the regulation of gene expression was specific for NolA and $NodD_2$.

$NolA_1$-LacZ, $NolA_2$-LacZ or $NolA_3$-LacZ fusions were assayed as a function of population density. The results indicated that only $NolA_1$ expression is cell-density dependent and required for $NodD_2$ expression (FIG. 11B).

EXAMPLE 9

Isolation of Cell Density Factor (Quorum Factor) from *B. japonicum* Conditioned Medium

Figure 12:
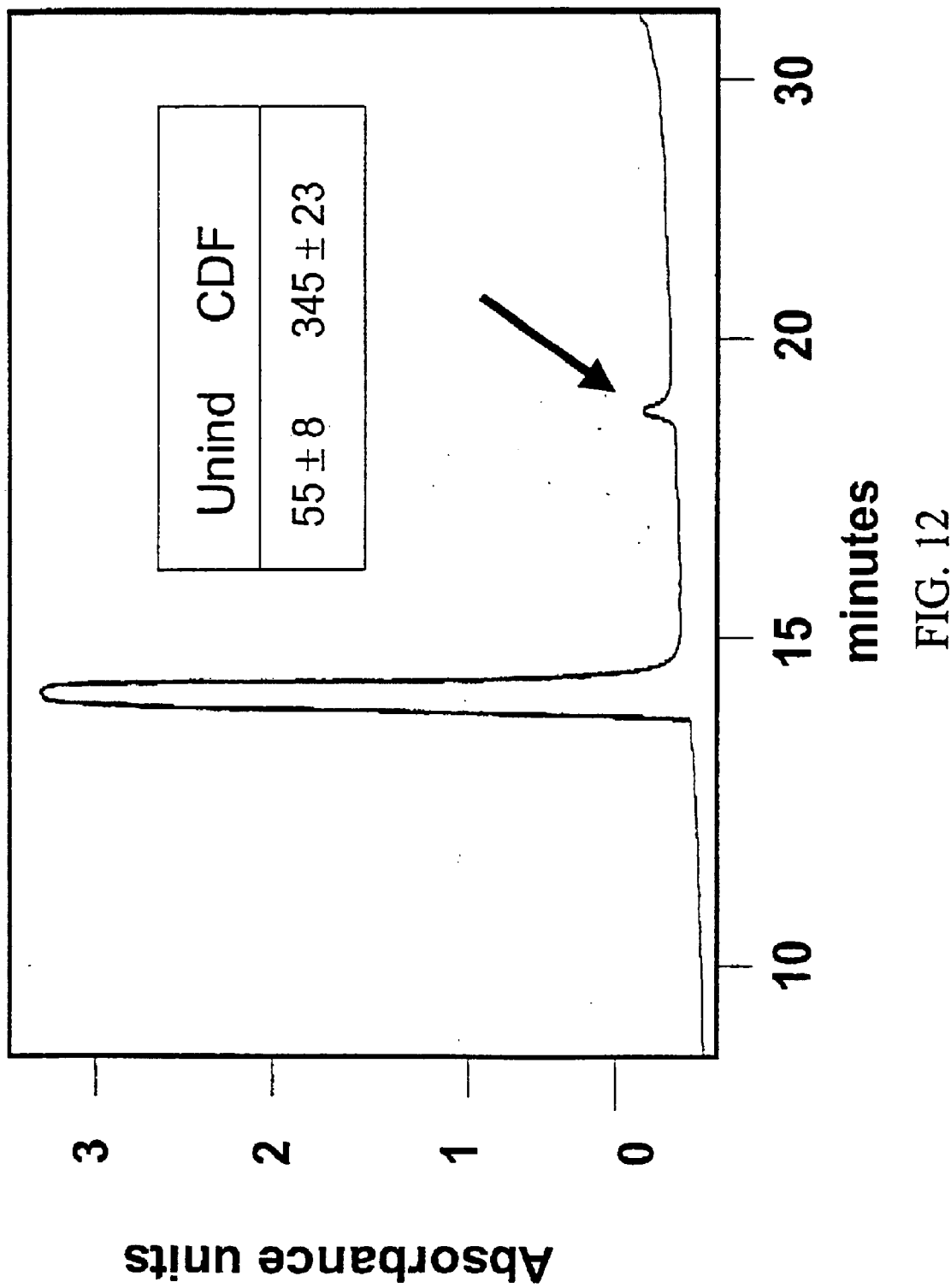
Figure 13:
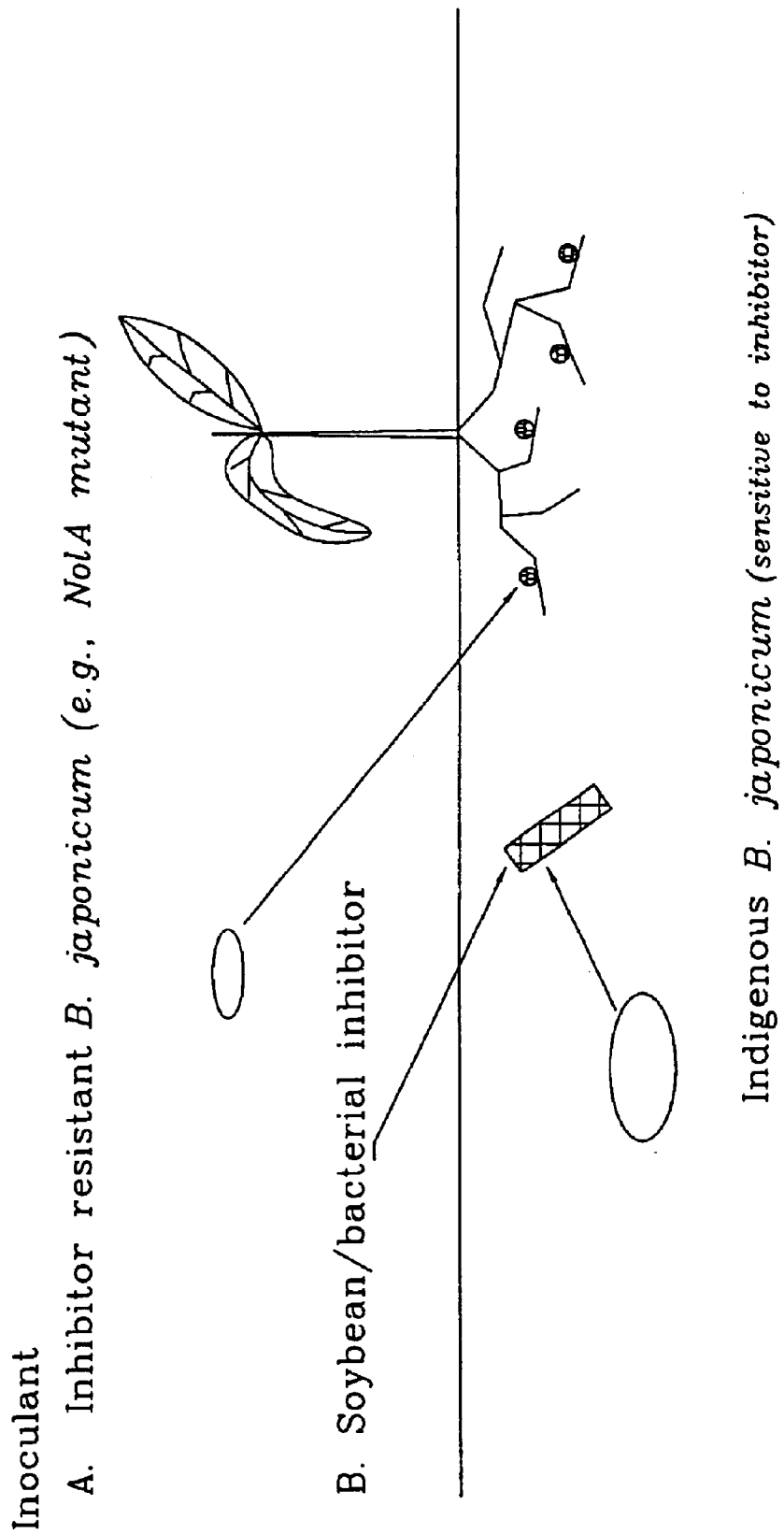

*B. japonicum* conditioned medium was concentrated approximately 10-fold. The material was then applied to a C18 column (Phenomenex, Inc., Torrance, Calif.) and eluted with a methanol gradient (0–100%) at a flow rate of 1 mL per minute. The HPLC elution profile is shown in FIG. 12. Cell density factor was demonstrated to be a potent inducer of nolA expression.

EXAMPLE 10

Effect of $Fe^{3+}$ on Nodulation Activity

Figure 14A:
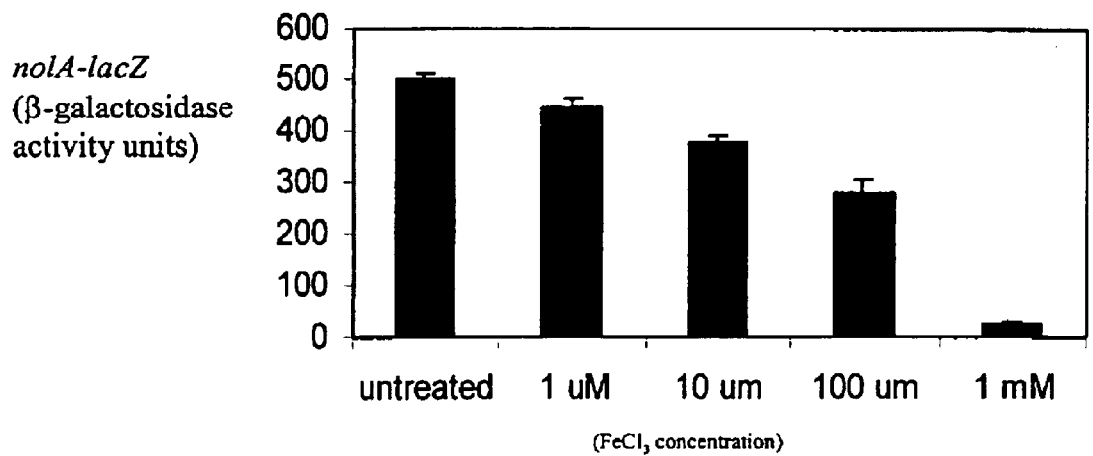
Figure 14B:
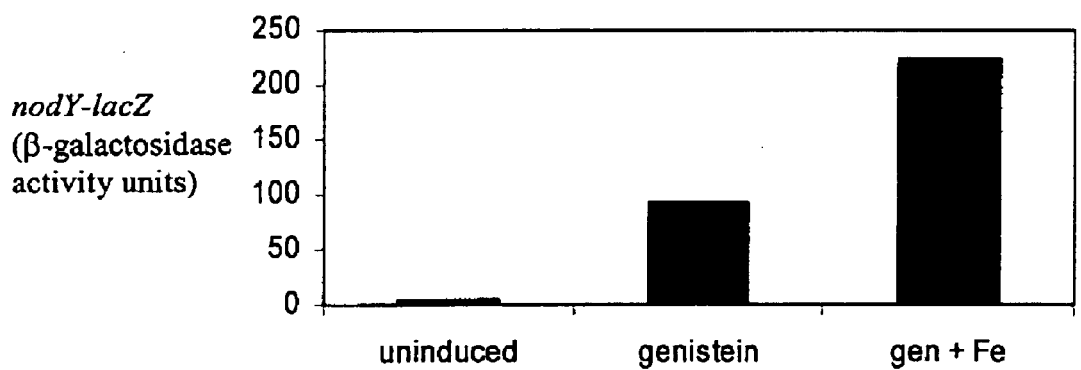

Analyses of CDF production revealed decreased levels of CDF in cultures grown in the presence of iron. As shown in FIG. 14A, the addition of $Fe^{3+}$ to *B. japonicum* cultures significantly reduced the expression of nolA expression at high culture densities. Consistent with the fact that nolA is involved in the repression of the nodulation genes, a corresponding increase in nodY-lacZ expression was also noted (FIG. 14B) when $Fe^{3+}$ was added to *B. japonicum* cultures. These results indicate that $Fe^{3+}$ can inhibit CDF production and, therefore, reduce the negative effect of quorum regulation on *B. japonicum* nod gene expression.

EXAMPLE 11

Recombinantly or UV Produced Mutants

We have generated, by recombinant means, mutations in the nwsB gene. The NwsB mutant appears to be defective in the recognition of the quorum signal and we have performed plant tests with the mutant in competition assays with the wild-type bacteria. In these assays, the effect of IND-1 (BEHP) on the ability of the NwsB mutant to nodulate soybean in the presence of wild-type bacteria (at different cell ratios) was examined. The NwsB strain should have a competitive advantage due to the lack of nod gene repression since it does not respond to the quorum signal. Nodule occupancy was scored both above (treated area) and below (new root growth) the root tip mark at the time of inoculation. As shown in FIG. 15, the addition of BEHP did increase the percentage of nodules that were occupied by the NwsB mutant. These studies were conducted using 25 µM levels of BEHP.

Another means to generate a mutant similar to NwsB is by UV mutagenesis. A commercial strain, such as *B. japonicum* Bj61A273, is transformed with a conjugative plasmid containing the nolA gene fused to the lacZ gene, encoding β-galactosidase. The latter is a reporter enzyme that allows the detection of NolA expression by formation of blue color on plates containing the chemical X-Gal. UV treated *B. japonicum* cells harboring a nolA-lacZ fusion are screened and selected for colonies that remain white on agar containing X-gal and inducing levels of the BEHP. To test whether an NwsB mutant has been isolated, complementation studies with the mutant and the nwsB gene will be conducted.

Figure 16:
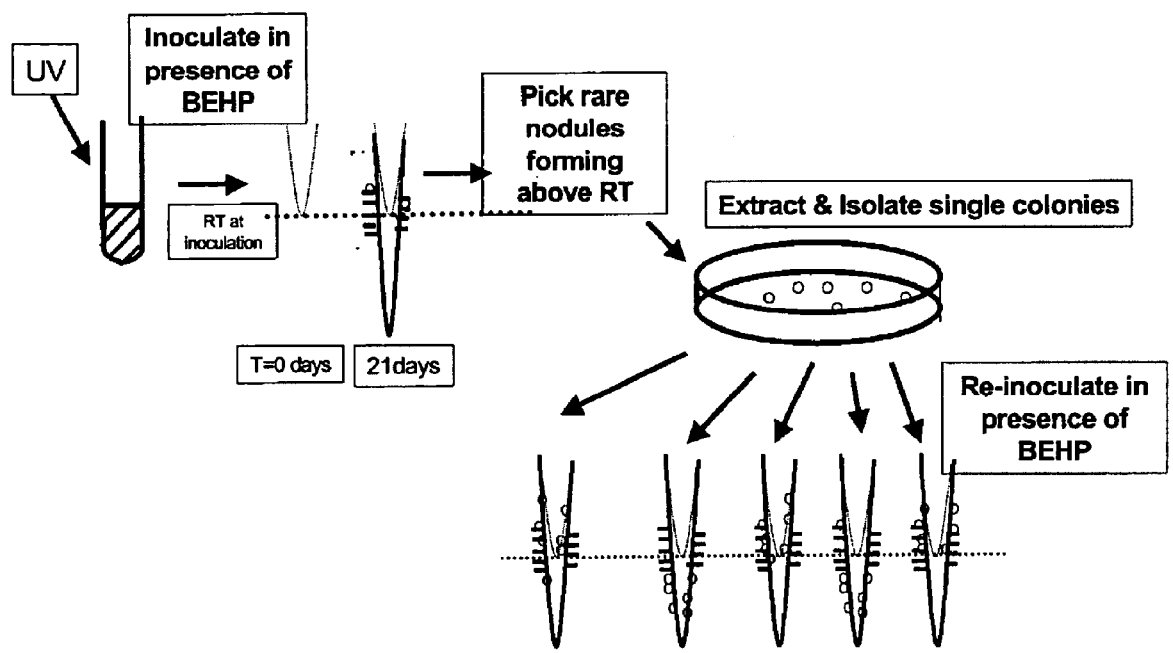
FIG. 16 shows a mutant selection scheme for the isolation of *B. japonicum* mutants that nodulate in the presence of inhibitory concentrations of BEHP.

Alternatively *B. japonicum* mutants can be isolated using the soybean plant as the means of selecting strains that are resistant to BEHP (FIG. 16). UV treated USDA61 A2 73 cells were inoculated onto soybean roots in the presence of BEHP. Most of the nodules formed in the UV treated samples demonstrated a delayed nodule phenotype in the presence of BEHP (i.e., below the root tip mark at the time of inoculation). Nodules formed above the root tip mark were extracted for bacteria. Single colonies have been isolated and are being re-screened for their ability to nodulate soybean plants in the presence of BEHP. In addition, these colonies are being transformed with the nolA-lacZ plasmid, and will be tested for BEHP mediated nolA-lacZ activity.

EXAMPLE 12

CDF-like Molecules Found in Other Organisms

Other rhizobia have been tested for the production a compound similar to the B. japonicum CDF. The B. japonicum nolA-lacZ fusion was used as a reporter system to test culture supernatants from a variety of bacteria. The assay system has been described above in Examples 2–6.

Figure 17:
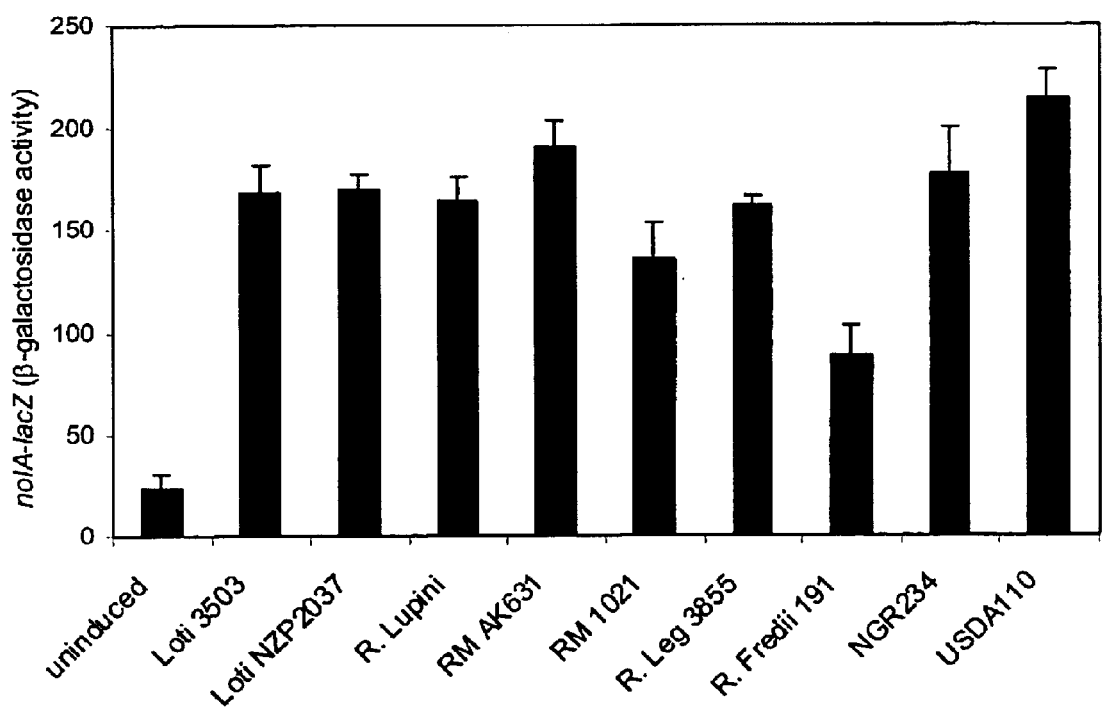

As shown in FIG. 17, we found that supernatants from rhizobial strains tested were able to induce the nolA-lacZ fusion. This indicates that compounds similar to CDF present in these cultures. R. lupini and S. meliloti were assayed for, and demonstrated to possess, a CDF-like molecule by examining the HPLC retention times of the active component (data not shown) in culture supernatants. In both cases, the active component exhibited a similar retention time to the B. japonicum CDF.

The presence of CDF-like molecules expressed by other bacteria has been analyzed using nolA-lacZ expression systems as a bioassay. These results are shown in FIG. 18.

It should be understood that the examples and embodiments described herein are for illustrative purposes only and that various modifications or changes in light thereof will be suggested to persons skilled in the art and are to be included within the spirit and purview of this application. All documents, patents, patent applications, and references cited within this application are hereby incorporated by reference in their entireties.

TABLE 1

Induction of nolA-Lac expression by extracts of commercial inoculants.

| | | β-galactosidase activity (U) | | |
|---|---|---|---|---|
| Uninduced | Untreated peat | Urbana Labs #J168 | Urbana Labs #196 | Lipha Tech |
| 83 ± 22 | 109 ± 18 | 438 ± 10 | 521 ± 43 | 356 ± 26 |

TABLE 2

Expression of nolA- and nodD$_2$-lacZ fusions in response to the population density dependent factor

| | β-galactosidase activity (U) | | |
|---|---|---|---|
| LacZ fusion | Uninduced | CM[a] | CM[b] (heat) |
| NolA$_{1,2,3}$-lacZ | 22 ± 2 | 300 ± 25 | 292 ± 22 |
| NolA$_1$-LacZ | 35 ± 3 | 205 ± 19 | 225 ± 18 |
| NolA$_2$-lacZ | 24 ± 4 | 42 ± 5 | 39 ± 5 |
| NolA$_3$-lacZ | 38 ± 6 | 62 ± 4 | 59 ± 8 |
| NodD$_2$-lacZ | 58 ± 14 | 393 ± 11 | 356 ± 16 |

[a]CM = conditioned medium from B. japonicum culture (A600 = 1.0).
[b]CM = (heat) = conditioned medium treated for 10 minutes at 100° C.
Units with CPRG as a substrate. Values are the means of two independent determinations. the standard deviation is indicated.

TABLE 3

Effect of population density dependent factor on the induction of nodY-lacZ in B. japonicum by genistein

| | β-galactosidase activity (U) | | |
|---|---|---|---|
| Uninduced | genistein[c] | genistein[c] +CM[a] | genistein[c] +CM[ab] (heat) |
| 3 ± 0 | 366 ± 11 | 33 ± 5 | 23 ± 5 |

[a]CM = conditioned medium from B. japonicum culture (A600 = 1.0).
[b]CM = (heat) = conditioned medium treated for 10 minutes at 100° C.
[c]cultures induced with 0.05 μM genistein for 5 h.
Units with CPRG as a substrate. Values are the means of two independent determinations. the standard deviation is indicated.

We claim:

1. A method of more efficiently nodulating a target plant species comprising producing a nodulation inoculant comprising culturing at least one strain of Bradyrhizobium japonicum in a liquid medium wherein the medium comprises a sufficient amount of iron to reduce the amount of Cell Density Factor (CDF) expression and then applying said inoculant to a target plant, parts of a target plant, or seeds thereof.

2. The method according to claim 1, wherein said at least one strain is Bradyrhizobium japonicum USDA 110.

3. The method according to claim 1, wherein said at least one strain is Bradyrhizobium japonicum USDA 123.

4. A method of more efficiently nodulating a target plant species comprising the steps of:

a) producing a nodulation inoculant by culturing at least one strain of Bradyrhizobium japonicum in a liquid medium wherein the medium comprises a sufficient amount of iron to reduce the amount of Cell Density Factor (CDF) expression;

b) incorporating said nodulation inoculant into soil; and c) and then applying seed or plant material of said target plant to said soil.

5. The method according to claim 4, wherein said at least one strain is Bradyrhizobium japonicum USDA 110.

6. The method according to claim 4, wherein said at least one strain is Bradyrhizobium japonicum USDA 123.

7. A method of improving the efficiency of soil inoculation comprising producing a nodulation inoculant by culturing at least one strain of Bradyrhizobium japonicum in a liquid medium wherein the medium comprises a sufficient amount of iron to reduce the amount of Cell Density Factor (CDF) expression, applying said inoculant soil, and growing plants in said soil.

8. The method according to claim 7, wherein said at least one strain is Bradyrhizobium japonicum USDA 110.

9. The method according to claim 7, wherein said at least one strain is Bradyrhizobium japonicum USDA 123.

* * * * *

UNITED STATES PATENT AND TRADEMARK OFFICE
CERTIFICATE OF CORRECTION

PATENT NO. : 6,855,536 B2
DATED : February 15, 2005
INVENTOR(S) : John T. Loh and Gary Stacey It is certified that error appears in the above-identified patent and that said Letters Patent is hereby corrected as shown below:

Title page,
Item [57], ABSTRACT,
Line 2, "transcripts" should read -- transcription --
Line 4, "too" should read -- to --

Column 3,
Line 54, "hi Gram-negative" should read -- In Gram-negative --
Line 62, "*trifoli*" should read -- *trifolii* --

Column 4,
Line 4, "by. *viciae*" should read -- bv. *viciae* --

Signed and Sealed this

Ninth Day of August, 2005

JON W. DUDAS
*Director of the United States Patent and Trademark Office*